(12) United States Patent  (10) Patent No.: US 8,309,306 B2
Nolan et al.  (45) Date of Patent: Nov. 13, 2012

(54) DETECTION COMPOSITION

(75) Inventors: Garry Nolan, San Francisco, CA (US);
Philip McGarrigle, South San Francisco, CA (US)

(73) Assignee: Nodality, Inc., South San Francisco ( * ) Notice: Subject to any disclaimer, the term of this patent is extended or adjusted under 35 U.S.C. 154(b) by 302 days.

(21) Appl. No.: 12/617,438

(22) Filed: Nov. 12, 2009

(65) Prior Publication Data

US 2010/0151472 A1 Jun. 17, 2010

Related U.S. Application Data

(60) Provisional application No. 61/113,823, filed on Nov. 12, 2008.

(51) Int. Cl.
C12Q 1/68 (2006.01)
G01N 33/53 (2006.01)
C07H 21/02 (2006.01)
C07H 21/04 (2006.01)
C07K 1/00 (2006.01)
C07K 14/00 (2006.01)
C07K 17/00 (2006.01)
A61K 35/14 (2006.01)

(52) U.S. Cl. ........ 435/6.1; 435/7.1; 536/23.1; 536/24.3; 530/350; 530/386; 530/387.1

(58) Field of Classification Search .................... 435/6.1, 435/7.1; 536/23.1, 24.3, 350; 530/350, 386, 530/387.1
See application file for complete search history.

(56) References Cited

U.S. PATENT DOCUMENTS

| | | | |
|---|---|---|---|
| 4,421,735 A | 12/1983 | Haber et al. | |
| 4,469,863 A | 9/1984 | Ts'o et al. | |
| 4,816,567 A | 3/1989 | Cabilly et al. | |
| 5,034,506 A | 7/1991 | Summerton et al. | |
| 5,216,141 A | 6/1993 | Benner | |
| 5,225,539 A | 7/1993 | Winter | |
| 5,235,033 A | 8/1993 | Summerton et al. | |
| 5,292,658 A | 3/1994 | Cormier et al. | |
| 5,385,707 A | 1/1995 | Miltenyi et al. | |
| 5,386,023 A | 1/1995 | Sanghvi et al. | |
| 5,418,155 A | 5/1995 | Cormier et al. | |
| 5,530,101 A | 6/1996 | Queen et al. | |
| 5,585,089 A | 12/1996 | Queen et al. | |
| 5,602,240 A | 2/1997 | De Mesmaeker et al. | |
| 5,635,352 A * | 6/1997 | Urdea et al. | 435/6.18 |
| 5,637,684 A | 6/1997 | Cook et al. | |
| 5,644,048 A | 7/1997 | Yau | |
| 5,683,888 A | 11/1997 | Campbell | |

(Continued)

FOREIGN PATENT DOCUMENTS

WO  WO 92/15673 A1  9/1992

(Continued)

OTHER PUBLICATIONS

The Stratagene Catalog p. 39 (1988).*

(Continued)

*Primary Examiner* — Ethan C Whisenant
(74) *Attorney, Agent, or Firm* — Wilson Sonsini Goodrich & Rosati

(57) ABSTRACT

The invention provides methods, kits, devices and compositions for detecting one or more target analytes. In some embodiments, the invention provides binding elements and labeling elements capable of being joined through a plurality of joining elements.

27 Claims, 4 Drawing Sheets

U.S. PATENT DOCUMENTS

| | | |
|---|---|---|
| 5,686,071 A | 11/1997 | Subramanian et al. |
| 5,693,761 A | 12/1997 | Queen et al. |
| 5,693,762 A | 12/1997 | Queen et al. |
| 5,741,668 A | 4/1998 | Ward et al. |
| 5,777,079 A | 7/1998 | Tsien et al. |
| 5,804,387 A | 9/1998 | Cormack et al. |
| 5,821,337 A | 10/1998 | Carter et al. |
| 5,854,033 A | 12/1998 | Lizardi |
| 5,859,205 A | 1/1999 | Adair et al. |
| 5,874,304 A | 2/1999 | Zolotukhin et al. |
| 5,876,995 A | 3/1999 | Bryan |
| 5,925,558 A | 7/1999 | Tsien et al. |
| 5,968,738 A | 10/1999 | Anderson et al. |
| 6,020,210 A | 2/2000 | Miltenyi |
| 6,054,297 A | 4/2000 | Carter et al. |
| 6,060,246 A * | 5/2000 | Summerton et al. ......... 435/6.12 |
| 6,180,370 B1 | 1/2001 | Queen et al. |
| 6,261,771 B1 | 7/2001 | Bohannon |
| 6,287,778 B1 * | 9/2001 | Huang et al. ..................... 506/4 |
| 6,306,610 B1 | 10/2001 | Bawendi et al. |
| 6,316,186 B1 * | 11/2001 | Ekins .......................... 435/6.11 |
| 6,361,947 B1 | 3/2002 | Dong et al. |
| 6,407,213 B1 | 6/2002 | Carter et al. |
| 6,440,667 B1 | 8/2002 | Fodor et al. |
| 6,458,530 B1 | 10/2002 | Morris et al. |
| 6,495,333 B1 | 12/2002 | Willmann et al. |
| 6,514,767 B1 | 2/2003 | Natan |
| 6,576,428 B1 | 6/2003 | Assenmacher et al. |
| 6,686,461 B1 | 2/2004 | Schwartz et al. |
| 6,733,743 B2 | 5/2004 | Jordan |
| 6,806,047 B2 | 10/2004 | Goldberg et al. |
| 6,830,936 B2 | 12/2004 | Anderson et al. |
| 7,018,850 B2 | 3/2006 | Raymond et al. |
| 7,151,564 B2 | 12/2006 | Kubo |
| 7,294,298 B2 | 11/2007 | Iijima |
| 7,294,503 B2 | 11/2007 | Quake et al. |
| 7,378,280 B2 | 5/2008 | Quake et al. |
| 7,381,535 B2 | 6/2008 | Perez et al. |
| 7,393,656 B2 | 7/2008 | Perez et al. |
| 7,462,689 B2 | 12/2008 | Schwartz |
| 7,563,584 B2 | 7/2009 | Perez et al. |
| 7,732,628 B2 | 6/2010 | Schwartz et al. |
| 7,939,278 B2 | 5/2011 | Perez et al. |
| 8,026,051 B2 * | 9/2011 | Hyldig-Nielsen et al. ... 435/6.11 |
| 8,148,094 B2 | 4/2012 | Perez et al. |
| 8,198,037 B2 | 6/2012 | Perez et al. |
| 8,206,939 B2 | 6/2012 | Perez et al. |
| 2001/0006787 A1 | 7/2001 | Payan |
| 2002/0028431 A1 | 3/2002 | Julien |
| 2002/0064779 A1 * | 5/2002 | Landegren et al. ................ 435/6 |
| 2003/0133874 A1 * | 7/2003 | Roder ............................ 424/9.2 |
| 2003/0207300 A1 | 11/2003 | Matray et al. |
| 2004/0229284 A1 | 11/2004 | Luciw et al. |
| 2005/0118580 A1 * | 6/2005 | Merk et al. ........................ 435/6 |
| 2006/0046272 A1 | 3/2006 | Chow et al. |
| 2007/0003950 A1 | 1/2007 | Shen et al. |
| 2007/0009923 A1 | 1/2007 | Nolan et al. |
| 2007/0117188 A1 * | 5/2007 | DeAngelis et al. ............. 435/85 |
| 2007/0172827 A1 | 7/2007 | Murakami |
| 2007/0196868 A1 | 8/2007 | Perez et al. |
| 2007/0196869 A1 | 8/2007 | Perez et al. |
| 2007/0196870 A1 | 8/2007 | Perez et al. |
| 2008/0182262 A1 | 7/2008 | Perez et al. |
| 2008/0241865 A1 * | 10/2008 | Ohmiya et al. .................... 435/8 |
| 2008/0254489 A1 | 10/2008 | Perez et al. |
| 2009/0068681 A1 | 3/2009 | Perez et al. |
| 2009/0081699 A1 | 3/2009 | Perez et al. |
| 2009/0098594 A1 | 4/2009 | Fantl et al. |
| 2009/0269773 A1 | 10/2009 | Fantl et al. |
| 2009/0269800 A1 | 10/2009 | Covey et al. |
| 2009/0291458 A1 | 11/2009 | Cohen et al. |
| 2009/0307248 A1 | 12/2009 | Moser et al. |
| 2010/0009364 A1 | 1/2010 | Fantl et al. |
| 2010/0014741 A1 | 1/2010 | Banville et al. |
| 2010/0030719 A1 | 2/2010 | Covey et al. |
| 2010/0042351 A1 | 2/2010 | Covey et al. |
| 2010/0086951 A1 | 4/2010 | Hedley et al. |
| 2010/0092985 A1 * | 4/2010 | Lee et al. ........................... 435/6 |
| 2010/0099109 A1 | 4/2010 | Fantl et al. |
| 2010/0105074 A1 | 4/2010 | Covey et al. |
| 2010/0184092 A1 | 7/2010 | Perez et al. |
| 2010/0204973 A1 | 8/2010 | Parkinson et al. |
| 2010/0209929 A1 | 8/2010 | Fantl et al. |
| 2010/0215644 A1 | 8/2010 | Fantl et al. |
| 2010/0221750 A1 | 9/2010 | Perez et al. |
| 2010/0233733 A1 | 9/2010 | Fantl |
| 2010/0240542 A1 | 9/2010 | Soper et al. |
| 2010/0285594 A1 | 11/2010 | Purvis, Jr. |
| 2010/0297676 A1 | 11/2010 | Fantl et al. |
| 2011/0059861 A1 | 3/2011 | Nolan et al. |
| 2011/0104717 A1 | 5/2011 | Fantl et al. |
| 2011/0111973 A1 * | 5/2011 | Mecklenburg et al. ........... 506/9 |
| 2011/0201018 A1 | 8/2011 | Perez et al. |
| 2011/0201019 A1 | 8/2011 | Perez et al. |
| 2011/0207145 A1 | 8/2011 | Perez et al. |
| 2011/0207146 A1 | 8/2011 | Perez et al. |
| 2011/0207149 A1 | 8/2011 | Perez et al. |
| 2011/0250614 A1 | 10/2011 | Perez et al. |
| 2011/0262468 A1 | 10/2011 | Fantl et al. |
| 2011/0269154 A1 | 11/2011 | Fantl et al. |
| 2011/0269634 A1 | 11/2011 | Perez et al. |
| 2012/0070849 A1 | 3/2012 | Perez et al. |
| 2012/0157340 A1 | 6/2012 | Cesano et al. |

FOREIGN PATENT DOCUMENTS

| | | |
|---|---|---|
| WO | WO 94/24314 A1 | 10/1994 |
| WO | WO 95/07463 A1 | 3/1995 |
| WO | WO 98/26277 A2 | 6/1998 |
| WO | WO 98/14605 A1 | 9/1998 |
| WO | WO 98/26277 A3 | 6/1999 |
| WO | WO 99/49019 A2 | 9/1999 |
| WO | WO 99/54494 A2 | 10/1999 |
| WO | WO 99/54494 A3 | 2/2000 |
| WO | WO 99/49019 A3 | 6/2000 |
| WO | WO 03/067210 A2 | 8/2003 |
| WO | WO 03/067210 A3 | 12/2003 |
| WO | WO 2006/012507 A2 | 2/2006 |
| WO | WO 2006/012507 A3 | 10/2006 |
| WO | WO 2008/140452 A1 | 11/2008 |
| WO | WO 2009/025847 A2 | 2/2009 |
| WO | WO 2009/025847 A3 | 6/2009 |
| WO | WO 2010/006291 A1 | 1/2010 |
| WO | WO 2010/028277 A1 | 3/2010 |
| WO | WO 2010/045651 A1 | 4/2010 |
| WO | WO 2010/135608 A1 | 11/2010 |

OTHER PUBLICATIONS

Lee et al.,Seven-Color, Homogeneous Detection of Six PCR Products. Biotechniques 27 :342-349 (1999).*

Niemeyer et al., Fluorometric Polymerase Chain Reaction (PCR) Enzyme-Linked Immunosorbent Assay for Quantification of Immuno-PCR Products in Microplates. Analytical Biochemistry 246 : 140-145 (1997).*

U.S. Appl. No. 61/048,657, filed May 4, 2009, Covey et al.
U.S. Appl. No. 61/048,886, filed Apr. 29, 2008, Fantl et al.
U.S. Appl. No. 61/048,920, filed Apr. 29, 2008, Fantl et al.
U.S. Appl. No. 61/079,537, filed Jul. 10, 2008, Putta.
U.S. Appl. No. 61/079,766, filed Jul. 10, 2008, Fantl et al.
U.S. Appl. No. 61/085,789, filed Aug. 1, 2008, Fantl et al.
U.S. Appl. No. 61/104,666, filed Oct. 10, 2008, Nolan.
U.S. Appl. No. 61/106,462, filed Oct. 17, 2008, Fantl.
U.S. Appl. No. 61/108,803, filed Oct. 27, 2008, Covey.
U.S. Appl. No. 61/113,823, filed Nov. 12, 2008, Nolan et al.
U.S. Appl. No. 61/144,684, filed Jan. 14, 2009, Fantl et al.
U.S. Appl. No. 61/144,955, filed Jan. 15, 2009, Parkinson et al.
U.S. Appl. No. 61/146,276, filed Jan. 21, 2009, Parkinson et al.
U.S. Appl. No. 61/151,387, filed Feb. 10, 2009, Fantl et al.
U.S. Appl. No. 61/155,373, filed Feb. 25, 2009, Fantl.
U.S. Appl. No. 61/156,754, filed Mar. 2, 2009, Fantl et al.
U.S. Appl. No. 61/157,900, filed Mar. 5, 2009, Fantl.
U.S. Appl. No. 61/162,598, filed App Feb. 23, 2009, Covey et al.
U.S. Appl. No. 61/162,673, filed Mar. 23, 2009, Soper et al.
U.S. Appl. No. 61/170,348, filed Apr. 17, 2008, Fantl et al.
U.S. Appl. No. 61/176,420, filed May 7, 2009, Purvis.

U.S. Appl. No. 61/177,935, filed May 13, 2009, Fantl et al.
U.S. Appl. No. 61/181,211, filed May 26, 2009, Covey et al.
U.S. Appl. No. 61/182,518, filed May 29, 2009, Fantl et al.
U.S. Appl. No. 61/182,638, filed May 29, 2009, Fantl et al.
U.S. Appl. No. 61/186,619, filed Jun. 12, 2009, Fantl et al.
U.S. Appl. No. 61/216,825, filed May 20, 2009, Fantl et al.
U.S. Appl. No. 61/218,718, filed Jun. 19, 2009, Fantl et al.
U.S. Appl. No. 61/226,878, filed Jul. 20, 2009, Fantl et al.
Altman, et al. Phenotypic analysis of antigen-specific T lymphocytes. Science, 1996;274(5284):94-6.
Bailey, et al. DNA-encoded antibody libraries: a unified platform for multiplexed cell sorting and detection of genes and proteins. J AM Chem Soc. 2007;129(7):1959-67.
Barn, et al. Design and synthesis of a maximally diverse and druglike screening library using REM resin methodology. J Comb Chem. 2001;3(6):534-41.
Beaucage, et al. The functionalization of oligonucleotides via phosphoramidite derivative. Tetrahedron. 1993;49(10):1925-63.
Blume, et al. Oncogenic kinase signalling. Nature. 2001;411(6835):355-65.
Boer, et al. Prostaglandin-E2 enhances EPO-mediated STAT5 transcriptional activity by serine phosphorylation of CREB. Blood. 2002;100(2):467-73.
Brill, et al. Synthesis of oligodeoxynucleoside phosphorodithioates via thioamidites. J. Am. Chem. Soc. 1989;111:2321-2322.
Carlsson, et al. Screening for genetic mutations. Nature. 1996;380(6571):207.
Carter, et al. Humanization of an anti-p185HER2 antibody for human cancer therapy. Proc Natl Acad Sci U S A. 1992;89(10):4285-9.
Chalfie, et al. Green fluorescent protein as a marker for gene expression. Science. 1994;263(5148):802-5.
Chattopadhyay, et al. Quantum dot semiconductor nanocrystals for immunophenotyping by polychromatic flow cytometry. Nat Med. 2006;12(8):972-7.
Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001;46(2):72-8.
Clark, M. Antibody humanization: a case of the 'Emperor's new clothes'? Immunol. Today. 2000;21(8):397-402.
Cochran, et al. A minimal peptide scaffold for beta-turn display: optimizing a strand position in disulfide-cyclized beta-hairpins. J Am Chem Soc. 2001;123(4):625-32.
Crans-Vargas, et al. CREB as a prognostic marker in acute leukemia. Abstract. Blood. 2001; 98(11), part 1, p. 316a.
Demirci, et al. Direct etch method for microfluidic channel and nanoheight post-fabrication by picoliter droplets. Applied Physics Letters. 2006; 88 (5):053117.
Dempcy, et al. Synthesis of a thymidyl pentamer of deoxyribonucleic guanidine and binding studies with DNA homopolynucleotides. Proc Natl Acad Sci USA. 1995;92(13):6097-101.
Dierck, et al. Quantitative multiplexed profiling of cellular signaling networks using phosphotyrosine-specific DNA-tagged SH2 domains. Nat Methods. 2006;3(9):737-44.
Dirksen, et al. Nucleophilic catalysis of hydrazone formation and transimination: implications for dynamic covalent chemistry. J Am Chem Soc. Dec. 13, 2006;128(49):15602-3.
Dirksen, et al. Nucleophilic catalysis of oxime ligation. Angew Chem Int Ed Engl. Nov. 20, 2006;45(45):7581-4.
Dirksen, et al. Rapid oxime and hydrazone ligations with aromatic aldehydes for biomolecular labeling. Bioconjug Chem. Dec. 2008;19(12):2543-8.
Egholm, et al. Peptide nucleic acids (PNA) oligonucleotide analogues with an achiral peptide backbone. J. Am. Chem. Soc. 1992;114:1895-1897.
Egholm, et al. PNA hybridizes to complementary oligonucleotides obeying the Watson-Crick hydrogen-bonding rules. Nature. 1993;365(6446):566-8.
European search report and search opinion dated Feb. 22, 2011 for Application No. 10180167.8.
Fredriksson, et al. Multiplexed protein detection by proximity ligation for cancer biomarker validation. Nat Methods. Apr. 2007;4(4):327-9.
Gao, et al. Unusual conformation of a 3'-thioformacetal linkage in a DNA duplex. J Biomol NMR. Jan. 1994;4(1):17-34.
Goldman, et al. Avidin: a natural bridge for quantum dot-antibody conjugates. J Am Chem Soc. 2002;124(22):6378-82.
Griffiths, et al. Strategies for selection of antibodies by phage display. Curr Opin Biotechnol. 1998;9(1):102-8.
Gualillo, et al. Leptin promotes the tyrosine phosphorylation of SHC proteins and SHC association with GRB2. Mol Cell Endocrinol. 2002;190(1-2):83-9.
Gururaja, et al. A novel artificial loop scaffold for the noncovalent constraint of peptides. Chem. Biol. 2000;7:515-27.
Hanahan, et al. The Hallmarks of Cancer. Cell. 2000;100(1) 57-70.
Hauser, et al. Utilising the left-helical conformation of L-DNA for analysing different marker types on a single universal microarray platform. Nucleic Acids Res. 2006;34(18):5101-11.
Heim, et al. Engineering green fluorescent protein for improved brightness, longer wavelengths and fluorescence resonance energy transfer. Curr Biol. 1996;6(2):178-82.
Horn, et al. Oligonucleotides with alternating anionic and cationic phosphoramidate linkages: Synthesis and hybridization of stereouniform isomers. Tetrahedron Lett. 1996;37:743-746.
Houimel, et al. Functional inhibition of CCR3-dependent responses by peptides derived from phage libraries. Eur. J. Immunol. 2001;31:3535-45.
Houimel, et al. Selection of peptides and synthesis of pentameric peptabody molecules reacting specifically with ErbB-2 receptor. 2001;92(5):748-55.
Ichiki, et al. Regulation of the expression of human C epsilon germline transcript. Identification of a novel IL-4 responsive element. J Immunol. 1993;150(12):5408-17.
Irimia, et al. Universal microfluidic gradient generator. Anal Chem. 2006;78(10):3472-7.
Irish, et al. FLt3 ligand Y591 duplication and Bcl-2 over expression are detected in acute myeloid leukemia cells with high levels of phosphorylated wild-type p53. Neoplasia. 2007;109(6):2589-96.
Irish, et al. Mapping normal and cancer cell signaling networks: towards single-cell proteomics. Nature. 2006;6:146-155.
Irish, et al. Single cell profiling of potentiated phospho-protein networks in cancer cells. Cell. 2004;118:I-20.
Jenkins, et al. The biosynthesis of carbocyclic nucleosides. Chem. Soc. Rev. 1995;169-176.
Jones, et al. Replacing the complementarity-determining regions in a human antibody with those from a mouse. Nature. 1986;321:522-25.
Ju, et al. Imprinted polymers as tools for the recovery of secondary metabolites produced by fermentation, Biotechnol Bioeng. 1999;64(2):232-9.
Kiedrowski, et al. Parabolic growth of a self-replicating hexadeoxynucleotide bearing a 3'-5'-phosphoamidate linkage. Angew. Chem. Intl. Ed. English 1991;30:423-426.
Kindler, et al. Indentification of a novel activating mutation (Y842C) within the activation loop of FLT3 in a patient with AML. Abstract 4681. Blood. 2003; 102(11):239B-240B and 45th Annual Meeting of the American Society of Hematology. San Diego, CA, USA. Dec. 6-9, 2003.
Kornblau, et al. Dynamic single-cell network profiles in acute myelogenous leukemia are associated with patient response to standard induction therapy. Clin Cancer Res. Jul. 15, 2010;16(14):3721-33. (abstract).
Krutzik, et al. Analysis of protein phosphorylation and cellular signaling events by flow cytometry: techniques and clinical applications. Clinical Immunology. 2004; 110: 206-21.
Krutzik, et al. Coordinate analysis of murine immune cell surface markers and intracellular phosphoproteins by flow cytometry. J Immunol. 2005;175(4):2357-65.
Krutzik, et al. High-content single-cell drug screening with phosphospecific flow cytometry. Nat Chem Biol. 2008;4(2):132-42.
Krutzik, et al. Intracellular phospho-protein staining techniques for flow cytometry: monitoring single cell signaling events. Cytometry A. 2003;55(2):61-70.
Krutzik, et al. Characterization of the murine immunological signaling network with phosphospecific flow cytometry. J Immunol. 2005;175(4):2366-73.

Kurreck, J. Antisense technologies. Improvement through novel chemical modifications. Eur J Biochem. 2003;270(8):1628-44.

Letsinger, et al. Cationic oligonucletides. J. Am Chem. Soc. 1988; 110:4470-4471.

Letsinger, et al. Effects of pendant groups at phosphorus on binding properties of d-ApA analogues. Nucleic Acids Res. 1986;14(8):3487-99.

Letsinger, et al. Phosphoramidate analogs of oligonucleotides. J Org Chem. 1970;35(11):3800-3.

Lou, et al. Polymer-Based Elemental Tags for Sensitive Bioassays. Angew. Chem. Int. Ed. 2007;46: 6111-6114.

Mag, et al. Synthesis and selective cleavage of an oligodeoxynucleotide containing a bridged internucleotide 5'-phosphorothioate linkage. Nucleic Acids Res. 1991;19(7):1437-41.

Marvin et al. Normal bone marrow signal transduction profiles: a requisite for enhanced detection of signaling dysregulations in AML. Blood. Jan. 13, 2011. doi:10.1182/blood-2010-10-316026 [Epub ahead of print].

Meier, et al. Peptide nuclieic acids (PNAs)—Unusual properties of nonionic oligonucleotide analogues. Chem. Int. Ed. Engl. 1992;31:1008-1010.

Ng, et al. Alternative nucleic acid analogues for programmable assembly; hybridization of LNA to PNA. Nano Lett. 2005;5(I):107-11.

Niemeyer, et al. Immuno-PCR: high sensitivity detection of proteins by nucleic acid amplification. Trends Biotechnol. 2005;23(4)208-16.

Nolan, et al. Fluorescence-activated cell analysis and sorting of viable mammalian cells based on beta-D-galactosidase activity after transduction of *Escherichia coli* lacZ. Proc Natl Acad Sci U S A. 1988;85(8);2603-7.

O'Connor, et al. Humanization of an antibody against human protein C and calcium-dependence involving framework residues. Protein Eng. 1998;11(4):321-8.

Ong, et al. Dendrimer enhanced immunosensors for biological detection. Anal. Chim. Acta. 2001;444:143-48.

Ornatsky, et al. Messenger RNA Detection in Leukemia Cell lines by Novel Metal-Tagged in situ Hybridization using Inductively Coupled Plasma Mass Spectometry. Translational Oncogenomics. 2006;1:1-9.

Ornatsky, et al. Multiple Cellular Antigen Detection by ICP-MS. J. Imm. Methods. 2006;(1-2):68-76.

Pathak, et al. Hydroxylated quantum dots as luminescent probes for in situ hybridization. J Am Chem Soc. 2001;123(17):4103-4.

Pauwels, et al. Biological activity of new 2-5A analogues. Chemica Scripta. 1986;26:141-9.

Perez, et al. LFA-1 signaling through p44/42 is coupled to perforin degranulation in CD56+CD8+ natural killer cells. Blood. Aug. 15, 2004;104(4):1083-93.

Perez, et al. Simultaneous measurement of multiple active kinase states using polychromatic flow cytometry. Nat Biotechnol. 2002; 20: 155-62.

Queen, et al. A humanized antibody that binds to the interleukin 2 receptor. Proc Natl Acad Sci U S A. 1989;86(24):10029-33.

Rawls, R. Optimistic about antisense. Promising clinical results and chemical strategies for further improvements delight antisense drug researchers. C & E News, Jun. 2, 1997; 35-59.

Remacle, et al. Architecture with designer atoms: simple theoretical considerations, Proc Natl Acad Sci U S A. Jan. 18, 2000;97(2):553-8.

Riechmann, et al. Reshaping human antibodies for therapy. Nature. 1988;332:323-27.

Rosen, et al. Functional characterization of FLT3 receptor signaling deregulation in acute myeloid leukemia by single cell network profiling (SCNP). PLoS One. Oct. 27, 2010;5(10):e13543.

Sanghvi, et al. ed. Chapters 2 and 3, ASC Symposium Series 580—Carbohydrates Modifications in Antisense Research. American Chemical Society. Washington, DC. 1994.

Sanz, et al. Single-chain antibody-based gene therapy: inhibition of tumor growth by in situ production of phage-derived human antibody fragments blocking functionally active sites of cell-associated matrices. Gene Therapy. 2002;9(15):1049-53.

Sawai, et al. Synthesis and properties of oligoadenylic acids containing 2'-5' phosphoramide linkage, Chem. Lett. 1984; 805-808.

Schulz, et al. Single-cell phospho-protein analysis by flow cytometry. Curr Protoc Immunol. 2007;8:8.17.1-20.

Shankar, et al. CREB is amplified in AML blasts and is associated with an increased risk of relapse and decreased event-free survival. Abstract. Blood. 2004; 104(11), Part 1, p. 166A.

Shankar, et al. Role of cyclic AMP response element binding protein in human leukemias. Cancer. Nov. 1, 2005;104(9):1819-24.

Shankar, et al. The role of CREB as a proto-oncogene in hematopoiesis and in acute myeloid leukemia. Cancer Cell. Apr. 2005:7(4):351-62.

Spiekermann, et al. Overexpression and constitutive activation of FLT3 induces STAT5 activation in primary acute myeloid leukemia blast cells. Clinical Cancer Research. Jun. 2003; 9:2140-2150.

Sprinzel, et al. Enzymatic incorporation of ATP and CTP analogues into the 3' end of tRNA. Eur J Biochem, 1977;81(3):579-89.

Stauber, et al. Development and applications of enhanced green fluorescent protein mutants. Biotechniques. Biotechniques. 1998;24(3):462-6,468-71.

Stelzer, et al. Use of multiparameter flow cytometry and immunophenotyping for the diagnosis and classification of acute myeloid leukemia. In Immunophenotyping, Edited by Stewart et al. Wiley-Liss, Inc. 2000:215-238.

Stoeva, et al. Multiplexed detection of protein cancer markers with biobarcoded nanoparticle probes. J Am Chem Soc. 2006;128(26):8378-9.

Tanner, et al. Multiplex bio-assay with inductively coupled plasma mass spectrometry: Towards a massively multivariate single-cell technology. Spectrochimia Acta Part B. 2007; 62(3):188-95.

Tennila, et al. Peptide-oligonucleotide conjugates form stable and selective complexes with antibody and DNA. Bioconjug Chem. 2008;19(7):1361-7.

Tse, et al. Intracellular antibody capture technology: application to selection of intracellular antibodies recognising the BCR-ABL oncogenic protein. J Mol Biol. 2002;317(1):85-94.

UK office action and search report dated Feb. 22, 2011 for GB Application No. 1017857.2.

Van Hest, et al. Efficient introduction of alkene functionality into proteins in vivo. FEBS Lett. 1998;428:(1-2) 68-70.

Verhoeyen, et al. Reshaping human antibodies: grafting an antilysozyme activity. Science. 1988;239:1534-36.

Zhang, et al. Quantifying DNA-protein binding specificities by using oligonucleotide mass tags and mass spectroscopy. Proc Natl Acad Sci USA 2007;104(9):3061-6.

Zheng, et al. Regulation of STAT3 and STAT5 in the differentiation of FLT3/ITD expressing 32Dcl3 cells induced by G-CSF and CEP-701. Abstract 2935.Blood. 2002; 100(11) and 44th Annual Meeting of the American Society of Hematology. Philadelphia, PA, USA. Dec. 6-10, 2002.

Zhu, et al. Part-per-trillion level detection of estradiol by competitive fluorescence immunoassay using DNA/dye conjugate as antibody multiple labels. Analytica Chimica Acta. 2008;624(1):141-146.

Benekli, et al. Signal transducer and activator of transcription proteins in leukemias. Blood. Apr. 15, 2003;101(8):2940-54.

Birkenkamp, et al. Regulation of constitutive STAT5 phosphorylation in acute myeloid leukemia blasts. Leukemia. 2001; 15(12):1923-31.

Chow, et al. Constitutive phosphorylation of the S6 ribosomal protein via mTOR and ERK signaling in the peripheral blasts of acute leukemia patients. Experimental hematology. 2006; 34(9):1182-1190.

U.S. Appl. No. 13/384,181, filed Jan. 13, 2012, Cesano et al.

Antibody Labeling Kit. www.solulink.com. Drug Discovery & Development magazine. Oct. 2008; 11(10):9.

Chen, et al. Synthesis and in vitro Characterization of a Dendrimer-MORF Conjugate for Amplification Pretargeting. Bioconjug Chem. Aug. 2008;19(8):1518-25. Epub Jul. 23, 2008.

Faintuch, et al. Radiolabeled bombesin analogs for prostate cancer diagnosis: preclinical studies. Nuclear Medicine and Biology. 2008; 35:401-411.

Fella, et al. Amine-reactive pyridylhydrazone-based PEG reagents for pH-reversible PEI polyplex shielding. Eur J Pharm Sci. Aug. 7, 2008;34(4-5):309-20. Epub May 28, 2008.

Kalyuzhny, et al. Novel multi-color immunofluorescence technique using primary antibodies raised in the same host species. (Poster).

Presented on Oct. 20, 2009 at Society for Neuroscience Scientific Sessions 586.26. http://www.sfn.org/am2009/skins/main/pdf/final_program/final_program_b5.pdf.

Schwartz, et al. BIOL 052—Conjugation and immobilization of proteins, peptides and oligonucleotides mediated by a stable bis-arylhydrazone based on 6-hydrazinonicotinic acid. (Poster). Presented on Apr. 8, 2008. The 235th ACS National Meeting, New Orleans, LA, Apr. 6-10, 2008. http://oasys2.confex.com/acs/235nm/techprogram/P1159367.HTM.

SoluLink. 2007-2008 Catalog and reference manual. Next generation conjugation reagents and services. SoluLink the Conjugation company. 2007. 116 pages. www.solulink.com.

Amico, et al. Differential response of human acute myeloid leukemia cells to gemtuzumab ozogamicin in vitro: role of Chk1 and Chk2 phosphorylation and caspase 3. Blood. Jun. 1, 2003;101(11):4589-97.

Kumar, et al. 2-methoxyestradiol blocks cell-cycle progression at G(2)/M phase and inhibits growth of human prostate cancer cells. Mol Carcinog. Jul. 2001;31(3):111-24.

Mack, et al. Detection of caspase-activation in intact lymphoid cells using standard caspase substrates and inhibitors. J Immunol Methods. Jul. 31, 2000;241(1-2):19-31.

U.S. Appl. No. 13/094,735, filed Apr. 26, 2011, Perez et al.
U.S. Appl. No. 13/094,737, filed Apr. 26, 2011, Perez et al.
U.S. Appl. No. 13/453,636, filed Apr. 23, 2012, Purvis, Jr.
U.S. Appl. No. 13/464,254, filed May 4, 2012, Moser et al.
U.S. Appl. No. 13/473,829, filed May 17, 2012, Fantl et al.
U.S. Appl. No. 13/493,857, filed Jun. 11, 2012, Fantl et al.
U.S. Appl. No. 13/544,053, filed Jul. 9, 2012, Soper et al.

* cited by examiner

DETECTION COMPOSITION

CROSS-REFERENCE

This application claims the benefit of U.S. Provisional Application No. 61/113,823, filed Nov. 12, 2008, which application is incorporated herein by reference.

BACKGROUND OF THE INVENTION

In many biological assays, especially those measuring fluorescence, instruments are restricted to a small number of possible simultaneous analysis channels, wherein only one analyte can be measured per channel. The existing methods of directly conjugating molecular detection complexes (i.e. antibodies) with different measurable labels (i.e. fluorescent dyes) require a significant investment of time and reagents. As a result, it is economically undesirable for manufacturers to produce and carry all possible combinations of directly-conjugated detection complexes. To circumvent this problem, in the field of flow cytometry unlabeled primary antibodies are commonly used in combination with directly labeled, isotype-specific secondary antibodies, but this approach is limited by the number of unique antibody isotypes in the reaction. Accordingly, there is a need for a multiplex-compatible labeling method that will allow manufacturers to minimize the number of unique reagents that must be synthesized, while conferring greater flexibility to the end user in terms of the number of different assays that can be designed using a standard set of reagents.

It is therefore one object of the disclosed invention to provide a method of rapidly and specifically conjugating molecular probes with detectable labels in an efficient protocol, via a convenient reaction, using stable reagents and materials, for the benefit of the end user's purposes.

It is another object of the disclosed invention to provide a method of rapidly and specifically conjugating multiple classes of molecular probes with different detectable labels in a multiplex reaction.

It is another object of the disclosed invention to allow the above to be carried out with reagents that, as individual components, are more stable and develop the desired novel characteristics (binding and detection), upon appropriate combination at a time more proximal to the experimentation.

SUMMARY OF THE INVENTION

The invention provides methods, kits, devices and compositions for detecting one or more a target analytes.

In some embodiments, the invention provides composition comprising: (i) a binding element directed against an activatable element, where the binding element comprises a first joining element, where the first joining element comprises a first oligonucleotide attached to the binding element, and where the first oligonucleotide comprises a first complementary oligonucleotide region; (ii) a second joining element comprising a second oligonucleotide, where the second oligonucleotide comprises a labeling element, and where the second oligonucleotide comprises a second complementary oligonucleotide region; and (iii) a third joining element comprising a third oligonucleotide, where the third oligonucleotide comprises a third complementary oligonucleotide region and a fourth complementary oligonucleotide region, where the third complementary oligonucleotide region is complementary to the first complementary oligonucleotide region in the first joining element and where the fourth complementary oligonucleotide region is complementary to the second complementary oligonucleotide region in the second joining element.

In some embodiments, the invention provides compositions comprising: (i) a binding element directed against an activatable element, where the binding element comprises a first joining element, where the joining element comprises a first oligonucleotide attached to the binding element, and where the first oligonucleotide comprises a first complementary oligonucleotide region; and (ii) a second joining element comprising a second oligonucleotide, where the second oligonucleotide comprises a labeling element, and where the second oligonucleotide comprises a second complementary oligonucleotide region, where the second complementary oligonucleotide region is complementary to the first complementary oligonucleotide region is the first joining element.

In some embodiments, the binding element is a peptide, a polypeptide, an oligopeptide, or an antibody. In some embodiments, the joining elements are independently selected from the group consisting of DNA, peptide nucleic acids, RNA, leucine zippers, polymers, or peptide loops.

In some embodiments, more than one labeling elements are attached to the second joining element. In some embodiments, the labeling element is an element selected from the group consisting of small molecule fluorophores, proteinaceous fluorophores, radioisotopes, enzymes, antibodies, chemiluminescent molecules, biotin, streptavidin, digoxigenin, chromogenic dyes, luminescent dyes, phosphorous dyes, luciferase, magnetic particles, beta-galactosidase, amino groups, carboxy groups, maleimide groups, oxo groups and thiol groups, quantum dots, chelated or caged lanthanides, isotope tags, radiodense tags, electron-dense tags, radioactive isotopes, paramagnetic particles, agarose particles, mass tags, e-tags, nanoparticles, and vesicle tags. In some embodiments, the labeling element comprises an enzyme and precursor compound.

In some embodiments, the joining element is an oligonucleotide or a nucleic acid having about 10 to about 100 bases in length. In some embodiments, the first joining element is covalently attached to the binding element.

In some embodiments, the activatable element is a phosphoprotein.

In some embodiments, the invention provides methods for labeling a binding element comprising the steps of: (i) providing a binding element, where the binding element is directed against an activatable element; (ii) providing a first joining element and a second joining element, where the first joining element comprises a first oligonucleotide, where the first oligonucleotide comprises a first complementary oligonucleotide region, where the second joining element comprises a second oligonucleotide, where the second oligonucleotide comprises a labeling element, where the second oligonucleotide comprises a second complementary oligonucleotide region, and where the second complementary oligonucleotide region in the second joining element is complementary to the first complementary oligonucleotide region in the first joining element; (iii) attaching the first joining element to the binding element, and (iv) hybridizing the second complementary region in second joining element to the first complementary region in the first joining element such that a complex is formed between the binding element, the first joining element and the second joining element. In some embodiments, attaching comprises covalently attaching the first joining element to the binding element. In some embodiments, the activatable element is a phosphoprotein.

In some embodiments, the invention provides methods of detecting the presence or absence of an activatable element in a sample comprising the steps of: (i) providing a sample potentially containing the activatable element; (ii) providing a binding element, where the binding element is directed against the target activatable element; where the binding element comprises a first joining element and a second joining element, where the first joining element comprises a first oligonucleotide attached to the binding element, where the first oligonucleotide comprises a first complementary oligonucleotide region, where the second joining element comprises a second oligonucleotide, where the second oligonucleotide comprises a labeling element, where the second oligonucleotide comprises a second complementary oligonucleotide region, where the second complementary oligonucleotide region in the second joining element is complementary to the first complementary oligonucleotide region in the first joining element; and where the second complementary region in second joining element is hybridized to the first complementary region in the first joining element; (iii) contacting the sample with the binding element; and (iv) detecting the labeling element, where the labeling element is indicative of the presence or absence of the activatable element in the sample.

In some embodiments, the joining elements are independently selected from the group consisting of DNA, peptide nucleic acids, RNA, leucine zippers, polymers, or peptide loops.

In some embodiments, the second joining element comprises a plurality labeling element. In some embodiments, the labeling element is an element selected from the group consisting of small molecule fluorophores, proteinaceous fluorophores, radioisotopes, enzymes, antibodies, chemiluminescent molecules, biotin, streptavidin, digoxigenin, chromogenic dyes, luminescent dyes, phosphorous dyes, luciferase, magnetic particles, beta-galactosidase, amino groups, carboxy groups, maleimide groups, oxo groups and thiol groups, quantum dots, chelated or caged lanthanides, isotope tags, radiodense tags, electron-dense tags, radioactive isotopes, paramagnetic particles, agarose particles, mass tags, e-tags, nanoparticles, and vesicle tags. In some embodiments, the labeling element comprises an enzyme and precursor compound.

In some embodiments, the joining elements are oligonucleotides having about 10 to about 100 bases in length. In some embodiments, the first joining element is covalently attached to the binding element.

In some embodiments, the binding element is selected from the group consisting of a peptide, a polypeptide, an oligopeptide, a protein, an antibody, a nucleic acid, a peptide nucleic acid, a synthetic small molecule, a disaccharide, a trisaccharide, an oligosaccharide, a polysaccharide, a lipid, a steroid, and a phospholipid.

In some embodiments, the activatable element is a phosphoprotein.

In some embodiments, the methods further comprise detecting a plurality of activatable elements by a method comprising the steps of: (i) contacting the plurality of activatable elements with a plurality of binding elements, where each binding element in the plurality of binding elements is directed against an activatable element in the plurality of activatable elements, where each binding element in the plurality of binding elements comprises a first joining element and a second joining element, where the first joining element comprises a first oligonucleotide attached to the binding element, where the first oligonucleotide comprises a first complementary oligonucleotide region, where the second joining element comprises a second oligonucleotide, where the second oligonucleotide comprises a labeling element, where the second oligonucleotide comprises a second complementary oligonucleotide region, where the second complementary oligonucleotide region in the second joining element is complementary to the first complementary oligonucleotide region in the first joining element, where the second complementary region in second joining element is hybridized to the first complementary region in the first joining element, and where each binding element comprises a different labeling element; and (ii) detecting the labeling elements, where the labeling elements are indicative of the presence or absence of the activatable elements in the sample.

In some embodiments, the invention provides kits comprising: (i) a binding element directed against an activatable element, (ii) a first joining element, where the first oligonucleotide comprises a first complementary oligonucleotide region; (iii) a second joining element comprising a second oligonucleotide, where the second oligonucleotide comprises a labeling element, and where the second oligonucleotide comprises a second complementary oligonucleotide region; (iv) a third joining element comprising a third oligonucleotide, where the third oligonucleotide comprises a third complementary oligonucleotide region and a fourth complementary oligonucleotide region, where the third complementary oligonucleotide region is complementary to the first complementary oligonucleotide region in the first joining element and where the fourth complementary oligonucleotide region is complementary to the second complementary oligonucleotide region in the second joining element; and (v) instructions to form a complex between the binding element, the first joining element, the second joining element and the third joining element.

In some embodiments, the invention provides kits comprising: (i) a binding element directed against an activatable element, (ii) a first joining element, where the joining element comprises a first oligonucleotide, where the first oligonucleotide comprises a first complementary oligonucleotide region; (iii) a second joining element comprising a second oligonucleotide, where the second oligonucleotide comprises a labeling element, and where the second oligonucleotide comprises a second complementary oligonucleotide region, where the second complementary oligonucleotide region is complementary to the first complementary oligonucleotide region in the first joining element; and (iv) instructions to form a complex between the binding element, the first joining element, and the second joining element.

In some embodiments, the binding element is a peptide, a polypeptide, an oligopeptide, or an antibody.

In some embodiments, the joining elements are independently selected from the group consisting of DNA, peptide nucleic acids, RNA, leucine zippers, polymers, or peptide loops.

In some embodiments, more than one labeling elements are attached to the second joining element. In some embodiments, the labeling element is an element selected from the group consisting of small molecule fluorophores, proteinaceous fluorophores, radioisotopes, enzymes, antibodies, chemiluminescent molecules, biotin, streptavidin, digoxigenin, chromogenic dyes, luminescent dyes, phosphorous dyes, luciferase, magnetic particles, beta-galactosidase, amino groups, carboxy groups, maleimide groups, oxo groups and thiol groups, quantum dots, chelated or caged lanthanides, isotope tags, radiodense tags, electron-dense tags, radioactive isotopes, paramagnetic particles, agarose particles, mass tags, e-tags, nanoparticles, and vesicle tags. In some embodiments, the labeling element comprises an enzyme and precursor compound.

In some embodiments, the joining element is an oligonucleotide or a nucleic acid having about 10 to about 100 bases in length.

In some embodiments, the kits further comprise instructions to covalently attach the first joining element to the binding element. In some embodiments, the kits further comprise instructions to detect an activatable element in a sample.

In some embodiments, the activatable element is a phosphoprotein.

One embodiment of the present invention is a detection composition, comprising a binding element capable of binding a protein; a first joining element bound to the binding element in a conformation that allows binding to a second joining element; a labeling element; and a second joining element bound to the labeling element in a conformation that allows binding to the first joining element. Another embodiment of the present invention is a detection composition, comprising a binding element directed against a phosphoprotein; a first joining element comprising a nucleic acid bound to the binding element in a conformation that allows binding to another nucleic acid having a partially complementary sequence; a labeling element; a second joining element comprising a nucleic acid bound to the labeling element in a conformation that allows binding to a nucleic acid; a third joining element comprising a nucleic acid which is capable of binding to the first and second nucleic acid sequence under the appropriate hybridization conditions; wherein the first and the second nucleic acids are complementary and are capable of binding under the appropriate hybridization conditions. Further embodiments specify that there are 2, 3, 4, 5, 6, or more joining elements per binding element; that the joining elements comprise DNA, RNA, peptide nucleic acids, RNA thiophosphates, leucine zippers, polymers, or peptide loops, that the binding element is an antibody or a fragment thereof. A further embodiment specifies that the joining element is an oligonucleotide or a nucleic acid having more than 10, 12, 15, 17, 20, 25, 30, 35, 40, 45, 50, 75, 85 or 100 bases in length. Another embodiment has more than one detectable label connected to the binding element.

A further embodiment of the invention provides methods for labeling a protein during a flow cytometry experiment, comprising covalently attaching a first joining element to a monoclonal antibody, wherein the first joining elements comprises an oligonucleotide, and wherein said joining element is covalently attached at a site where the oligonucleotide is available for binding to a complementary oligonucleotide. In some embodiments, the antibody is directed to a phosphoprotein. A fluorophore having a second joining element is provided, wherein said second joining element comprises an oligonucleotide covalently attached to the fluorophore in a conformation that allows binding to another oligonucleotide. A third joining element is provided comprising an oligonucleotide that is complimentary to at least one first and at least one second oligonucleotide; wherein at least one of each of the first and the second oligonucleotides capable of binding to the third oligonucleotide under the appropriate hybridization conditions. In some embodiments, the methods further comprise selecting a plurality of target phosphoproteins to monitor in the flow cytometry experiment; selecting a plurality of antibodies directed against the phosphoprotein targets; and selecting a plurality of fluorophores to combine with the antibodies, where said fluorophores are selected to be combined with individual antibodies so that the antibodies will bind to their targets and that the fluorophores will be compatible and distinguishable from one another in the flow cytometry experiment. In some embodiments, the selected antibodies are joined with a selected fluorophore prior to contact with the phosphoprotein by hybridizing the third oligonucleotide to each of the first and second oligonucleotides.

The present invention is also a kit for flow cytometry analysis, comprising: a set of reagents comprising a plurality of binding elements directed against a plurality of phosphoproteins, a first set of joining elements comprising nucleic acids covalently attached to each binding element in a conformation that allows binding to a complimentary nucleic acids, each binding element has a different nucleic acid which is minimally cross hybridizing to other different nucleic acids in the set; a plurality of fluorophores; a second set of joining elements comprising nucleic acids covalently attached to the fluorophores in a conformation that allows binding to a complementary nucleic acid, each fluorophore has a different nucleic acid in the second set which are minimally cross hybridizing to other different nucleic acids in the set; and instructions to select a binding element and a labeling element to be reversibly attached after selecting a panel of phosphoproteins to be investigated in the flow cytometry analysis. The kit may also contain a third binding element to join the first and second binding elements.

In one embodiment of the invention, the labeling element is an element of the group consisting of small molecule fluorophores (e.g. AlexaFluor 488), proteinaceous fluorophores (e.g. phycoerythrin), radioisotopes, enzymes, antibodies, chemiluminescent molecules, biotin, streptavidin, digoxigenin, chromogenic dyes, luminescent dyes, phosphorous dyes, luciferase, magnetic particles, beta-galactosidase, amino groups, carboxy groups, maleimide groups, oxo groups and thiol groups, quantum dots, chelated or caged lanthanides, isotope tags (e.g. for inductively coupled plasma mass spectrometry), radiodense tags (e.g. gold particles), electron-dense tags (e.g. gold particles), radioactive isotopes (e.g. $^{111}$Indium), paramagnetic particles (e.g. iron oxide-impregnated beads), agarose particles, mass tags (e.g. for mass spectrometry), e-tags (e.g. for mass spectrometry), nanoparticles (e.g. for Raman spectroscopy), and vesicle tags.

In one embodiment of the invention, the binding element is selected from the group consisting of a peptide, a polypeptide, an oligopeptide, a protein, a antibody, an activation state-specific antibody, a phospho-specific antibody, an antibody fragment, an engineered antibody, an recombinant antibody, a monoclonal antibody, a polyclonal antibody, a chimeric antibody, a humanized antibody, an aglycosylated antibody, a deglycosylated antibody, a nonglycosylated antibody, an epitope-recognizing fragment of an antibody, an antibody immobilized using beads, a peptide comprising a recognition structure that binds to a target structure on a protein, a single-chain antibody fragment (scFv), a nucleic acid, a synthetic nucleic acid analog, a phosphorothioate nucleic acid, a locked nucleic acid, a peptide nucleic acid, a phosphoramide-containing nucleic acid, a single stranded nucleic acid, a double stranded nucleic acid, a hybrid molecule containing both double stranded and single stranded nucleic acids, a DNA molecule, a RNA molecule, a hybrid molecule containing any combination of deoxyribo- and ribonucleotides, a bacterial extract, a fungal extract, a plant extract, an animal extract, a synthetic small molecule, a disaccharide, a trisaccharide, an oligosaccharide, a polysaccharide, a lipid, a steroid, a phospholipid, a naturally occurring protein, an integrin, a SH2 domain, and a MHC tetramer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
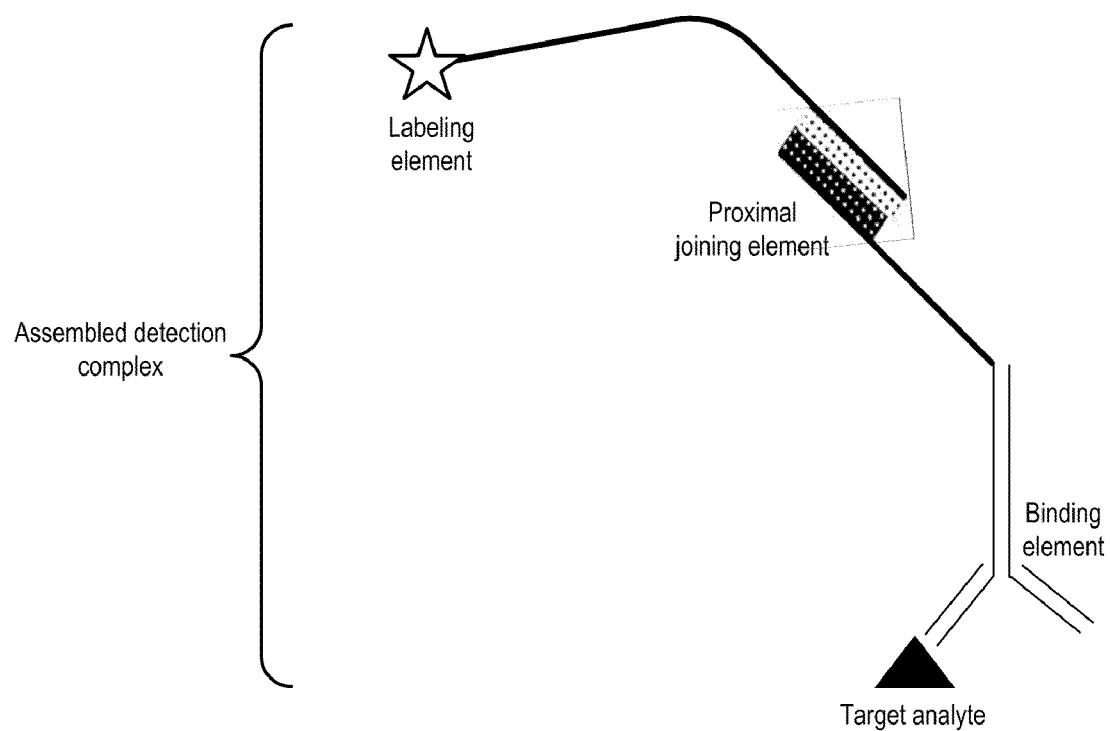
FIG. 1 shows the arrangement of one embodiment of the invention in which the binding element is joined to the labeling element through two joining elements.

Objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

All publications, patents, and patent applications mentioned in this specification are herein incorporated by reference to the same extent as if each individual publication or patent application was specifically and individually indicated to be incorporated by reference.

The present invention incorporates information disclosed in other patents, applications and texts. The following publications are hereby incorporated by reference in their entireties: Murphy and Janeway. Immunobiology. 7$^{th}$ Ed. Garland Publishing (2007); HPLC of Macromolecules: A Practical Approach, 2$^{nd}$ edition, Oxford University Press (1998); Current protocols in molecular biology, Ausubel et al, John Wiley & Sons, Inc. (2007); Genome Analysis: A Laboratory Manual Series (Vols. I-IV), Cold Spring Harbor Laboratory Press (1999); Antibodies: A Laboratory Manual, Cold Spring Harbor Laboratory Press (1988); Cells: A Laboratory Manual, Cold Spring Harbor Laboratory Press (1998); PCR Primer: A Laboratory Manual, Second Edition, Cold Spring Harbor Laboratory Press (2003); Stryer, L. Biochemistry, 4th Ed., Freeman, N.Y. (1995); Gait, "Oligonucleotide Synthesis: A Practical Approach", IRL Press, London (1984); Lehninger, Nelson and Cox, "Lehninger Principles of Biochemistry", 5th Ed., W.H. Freeman Pub., New York, N.Y. (2008); Berg et al., Biochemistry, 5th Ed., W.H. Freeman Pub., New York, N.Y. (2002); and Sambrook and Russell, "Molecular Cloning A laboratory Manual" 3rd Ed. Cold Spring Harbor Press (2001). The following patents and applications are also incorporated by reference. U.S. Pat. No. 6,458,530 (Selecting tag nucleic acids); U.S. Pat. No. 6,306,610 (Biological applications of quantum dots); U.S. Pat. No. 6,261,771 (Method and apparatus for detection of multiple nucleic acid sequences and multiple antigens); and U.S. Pat. No. 5,854,033 (Rolling circle replication reporter systems). United States Patent Applications: 2007/0003950 (Detecting targets by unique identifier nucleotide tags); 2004/0229284 (Multiplex analysis of proteins); 2003/0207300 (Multiplex analytical platform using molecular tags); and 2007/0172827 (Multiplex detection probes). The following relevant articles are incorporated by reference in their entireties: Bailey et al. DNA-encoded antibody libraries: a unified platform for multiplexed cell sorting and detection of genes and proteins. J Am Chem Soc (2007) vol. 129 (7) pp. 1959-67; Dierck et al. Quantitative multiplexed profiling of cellular signaling networks using phosphotyrosine-specific DNA-tagged SH2 domains. Nat Methods (2006) vol. 3 (9) pp. 737-744; Krutzik et al. Intracellular phospho-protein staining techniques for flow cytometry: Monitoring single cell signaling events. Cytometry (2003) vol. 55A (2) pp. 61-70; Niemeyer et al. Immuno-PCR: high sensitivity detection of proteins by nucleic acid amplification. Trends in Biotechnology (2005) vol. 23 (4) pp. 208-216; Stoeva et al. Multiplexed detection of protein cancer markers with biobarcoded nanoparticle probes. J Am Chem Soc (2006) vol. 128 (26) pp. 8378-9; Tang et al. DNA-directed assembly of protein microarrays. Front Biosci (2008) vol. 13 pp. 5755-71; Tennila et al. Peptide-oligonucleotide conjugates form stable and selective complexes with antibody and DNA. Bioconjug Chem (2008) vol. 19 (7) pp. 1361-7; Zhang et al. Quantifying DNA-protein binding specificities by using oligonucleotide mass tags and mass spectroscopy. Proc Natl Acad Sci USA (2007) vol. 104 (9) pp. 3061-6; and Zhu et al. Part-per-trillion level detection of estradiol by competitive fluorescence immunoassay using DNA/dye conjugate as antibody multiple labels. Analytica Chimica Acta (2008) vol. 624 (1) pp. 141-146.

The invention provides methods, compositions, kits and devices for detecting one or more target molecules. As disclosed herein, some embodiments of the present invention provide methods, kits, devices and compositions for attaching a detectable label to a binding element. It comprises providing a binding element and a labeling element, wherein both elements are capable of being joined through a plurality of joining elements which are capable of assembly when put in contact with each other using the appropriate conditions.

The disclosed compositions and methods make use of certain materials and procedures which allow specific labeling of binding elements. These materials and procedures are described in detail below. One embodiment of the invention allows the user to customize reagents thus creating more flexibility in reagent usage. This advantage provides the user with reagents that have a greater potential to be used more quickly and less likely to be kept on the shelf. Component inventory can be lower. Another advantage provides longer shelf life of the individual reagents over the combined reagent.

In some embodiments, some features of the disclosed methods, compositions, kits and devices are: 1. Using multiple pairs of complementary joining elements, multiple classes of binding elements can be labeled specifically in a single multiplexed reaction; 2. A bridging or additional joining element may be used to couple the labeling element to the binding element; 3. The hybridization operation may be performed before or after binding of the analyte by the binding element; and 4. An amplification operation may be performed before the hybridization operation to increase the sensitivity of the bioassay.

The term "Assembled Detection Complex" as used herein refers to the specific conjugation of one binding element to at least one labeling element by means of the specific binding of at least two joining elements.

The present invention provides uses for one or more reagents described herein. Examples of reagents that can also be used in the methods, compositions, kits and devices described herein are described in U.S. Pat. Nos. 7,381,535 and 7,393,656 and U.S. Ser. Nos. 10/193,462; 11/655,785; 11/655,789; 11/655,821; 11/338,957, 61/048,886; 61/048,920; 61/048,657; 61/079,766, and 61/085,789. Relevant articles include High-content single-cell drug screening with phosphospecific flow cytometry, Krutzik et al., Nature Chemical Biology, 23 Dec. 2007; Irish et al., FLt3 ligand Y591 duplication and Bcl-2 over expression are detected in acute myeloid leukemia cells with high levels of phosphorylated wild-type p53, Neoplasia, 2007, Irish et al. Mapping normal and cancer cell signaling networks: towards single-cell proteomics, Nature, Vol. 6 146-155, 2006; and Irish et al., Single cell profiling of potentiated phospho-protein networks in cancer cells, Cell, Vol. 118, 1-20 Jul. 23, 2004; Schulz, K. R., et al., Single-cell phospho-protein analysis by flow cytometry, Curr Protoc Immunol, 2007, 78:8 8.17.1-20; Krutzik, P. O., et al., Coordinate analysis of murine immune cell surface markers and intracellular phosphoproteins by flow cytometry, J Immunol 2005 Aug. 15; 175(4):2357-65; Krutzik, P. O., et al., Characterization of the murine immunological signaling network with phosphospecific flow cytometry, J Immunol. 2005 Aug. 15; 175(4):2366-73; Shulz et al., Current Protocols in Immunology 2007, 78:8.17.1-20; Stelzer et al. Use of Multiparameter Flow Cytometry and Immunophenotyping for the Diagnosis and Classfication of Acute Myeloid Leukemia, Immunophenotyping, Wiley, 2000; and Krutzik, P. O. and Nolan, G. P., Intracellular phospho-protein staining techniques for flow cytometry: monitoring single cell signaling events, Cytometry A. 2003 October; 55(2):61-70; Hanahan D., Weinberg, The Hallmarks of Cancer, CELL, 2000 Jan. 7; 100(1) 57-70; Krutzik et al, High content single cell drug screening with phophospecific flow cytometry, Nat Chem Biol. 2008 February; 4(2):132-42. Experimental and process protocols and other helpful information can be found at http:/proteomices.stanford.edu. The articles and other references cited above are incorporated by reference in their entireties for all purposes.

Binding Elements

The term "Binding element" includes any molecule (e.g., antibody, peptide, nucleic acid, small organic molecule) which is capable of specifically detecting the presence of an analyte.

In some embodiments, the binding element is a peptide, polypeptide, oligopeptide or a protein. The peptide, polypeptide, oligopeptide or protein may be made up of naturally occurring amino acids and peptide bonds, or synthetic peptidomimetic structures. Thus "amino acid", or "peptide residue", as used herein include both naturally occurring and synthetic amino acids. For example, homo-phenylalanine, citrulline and norleucine are considered amino acids for the purposes of the invention. The side chains may be in either the (R) or the (S) configuration. In some embodiments, the amino acids are in the (S) or L-configuration. If non-naturally occurring side chains are used, non-amino acid substituents may be used, for example to prevent or retard in vivo degradation. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. S218: U138 Part 2 Aug. 22, 1999, both of which are expressly incorporated by reference herein.

In some embodiments, the binding element is an antibody. In some embodiments, the binding element is an activation state-specific antibody. In some embodiments, the binding element is a phospho-specific antibody.

The term "antibody" includes full length antibodies and antibody fragments, and may refer to a natural antibody from any organism, an engineered antibody, or an antibody generated recombinantly for experimental, therapeutic, or other purposes as further defined below. Examples of antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. The term "antibody" comprises monoclonal and polyclonal antibodies. Antibodies can be antagonists, agonists, neutralizing, inhibitory, or stimulatory.

The antibodies of the present invention may be nonhuman, chimeric, humanized, or fully human. For a description of the concepts of chimeric and humanized antibodies see Clark et al., 2000 and references cited therein (Clark, (2000) Immunol. Today 21:397-402). Chimeric antibodies comprise the variable region of a nonhuman antibody, for example VH and VL domains of mouse or rat origin, operably linked to the constant region of a human antibody (see for example U.S. Pat. No. 4,816,567). In some embodiments, the antibodies of the present invention are humanized. By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) VL and VH frameworks (Winter U.S. Pat. No. 5,225,539). This strategy is referred to as "CDR grafting". "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213). The humanized antibody optimally also will comprise at least a portion of an immunoglobulin constant region, typically that of a human immunoglobulin, and thus will typically comprise a human Fc region. Methods for humanizing non-human antibodies are well known in the art, and can be essentially performed following the method of Winter and co-workers (Jones et al., 1986, Nature 321:522-525; Riechmann et al., 1988, Nature 332:323-329; Verhoeyen et al., 1988, Science, 239:1534-1536). Additional examples of humanized murine monoclonal antibodies are also known in the art, for example antibodies binding human protein C (O'Connor et al., 1998, Protein Eng 11:321-8), interleukin 2 receptor (Queen et al., 1989, Proc Natl Acad Sci, USA 86:10029-33), and human epidermal growth factor receptor 2 (Carter et al., 1992, Proc Natl. Acad Sci USA 89:4285-9). In an alternate embodiment, the antibodies of the present invention may be fully human, that is the sequences of the antibodies are completely or substantially human. A number of methods are known in the art for generating fully human antibodies, including the use of transgenic mice (Bruggemann et al., 1997, Curr Opin Biotechnol 8:455-458) or human antibody libraries coupled with selection methods (Griffiths et al., 1998, Curr Opin Biotechnol 9:102-108).

Specifically included within the definition of "antibody" are aglycosylated antibodies. By "aglycosylated antibody" as used herein is meant an antibody that lacks carbohydrate attached at position 297 of the Fc region, wherein numbering is according to the EU system as in Kabat. The aglycosylated antibody may be a deglycosylated antibody, which is an antibody for which the Fc carbohydrate has been removed, for example chemically or enzymatically. Alternatively, the aglycosylated antibody may be a nonglycosylated or unglycosylated antibody, that is an antibody that was expressed without Fc carbohydrate, for example by mutation of one or residues that encode the glycosylation pattern or by expression in an organism that does not attach carbohydrates to proteins, for example bacteria.

In some embodiments, an epitope-recognizing fragment of an antibody rather than the whole antibody is used. In some embodiments, the epitope-recognizing fragment is immobilized. In some embodiments, the antibody light chain that recognizes an epitope is used. A recombinant nucleic acid encoding a light chain gene product that recognizes an epitope may be used to produce such an antibody fragment by recombinant means well known in the art.

In some embodiments, antibodies are immobilized using beads analogous to those known and used for standardization in flow cytometry. Attachment of a multiplicity of antibodies to beads may be done by methods known in the art and/or described herein. Such conjugated beads may be contacted with sample, preferably cell extract, under conditions that allow for a multiplicity analytes, if present, to bind to the multiplicity of immobilized antibodies.

In alternative embodiments of the instant invention, aromatic amino acids of protein binding elements may be replaced with D- or L-naphylalanine, D- or L-phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole(alkyl)alanines, and D- or L-alkylalanines where alkyl may be substituted or unsubstituted methyl, ethyl, propyl, hexyl, butyl, pentyl, isopropyl, iso-butyl, sec-isotyl, iso-pentyl, and non-acidic amino acids of C1-C20.

Acidic amino acids can be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., —SO3H) threonine, serine, or tyrosine.

Other substitutions may include non-natural hydroxylated amino acids may made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Alkyl includes heteroalkyl, with atoms of nitrogen, oxygen and sulfur. In some embodiments, alkyl groups herein contain 1 to 12 carbon atoms. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the polypeptides may be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of variant polypeptides of to the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues.

Other suitable reagents for derivatizing alpha-amino-containing residues include compounds such as imidoesters, e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group. The specific modification of tyrosyl residues per se is well known, such as for introducing spectral labels into tyrosyl residues by reaction with aromatic diazonium compounds or tetranitromethane.

N-acetylimidizol and tetranitromethane may be used to form O-acetyl tyrosyl species and 3-nitro derivatives, respectively. Carboxyl side groups (aspartyl or glutamyl) may be selectively modified by reaction with carbodiimides (R'—N—C—N—R') such as 1-cyclohexyl-3-(2-morpholiny-1-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

In some embodiments, the binding element is a peptide comprising a recognition structure that binds to a target structure on a protein. A variety of recognition structures are well known in the art and can be made using methods known in the art, including by phage display libraries (see e.g., Gururaja et al. (2000) Chem. Biol. 7:515-27; Houimel et al., (2001) Eur. J. Immunol. 31:3535-45; Cochran et al. (2001) J. Am. Chem. Soc. 123:625-32; Houimel et al. (2001) Int. J. Cancer 92:748-55, each incorporated herein by reference).

A variety of recognitions structures are known in the art (e.g., Cochran et al., (2001) J. Am. Chem. Soc. 123:625-32; Boer et al., (2002) Blood 100:467-73, each expressly incorporated herein by reference)) and can be produced using methods known in the art (see e.g., Boer et al., (2002) Blood 100:467-73; Gualillo et al., (2002) Mol. Cell Endocrinol. 190:83-9, each expressly incorporated herein by reference)), including for example combinatorial chemistry methods for producing recognition structures such as polymers with affinity for a target structure on a protein (see e.g., Barn et al., (2001) J. Comb. Chem. 3:534-41; Ju et al., (1999) Biotechnol. 64:232-9, each expressly incorporated herein by reference). In some embodiments, the recognition structure is a single-chain antibody fragment (scFv) (see e.g., Sanz et al., (2002) Gene Therapy 9:1049-53; Tse et al., (2002) J. Mol. Biol. 317:85-94, each expressly incorporated herein by reference).

In some embodiments the binding element is also a nucleic acid. The term "nucleic acid" includes nucleic acid analogs, for example, phosphoramide (Beaucage et al., (1993) Tetrahedron 49(10):1925 and references therein; Letsinger, J. (1970) Org. Chem. 35:3800; Sprinzl et al., (1977) Eur. J. Biochem. 81:579; Letsinger et al., (1986) Nucl. Acids Res. 14:3487; Sawai et al, (1984) Chem. Lett. 805, Letsinger et al., (1988) J. Am. Chem. Soc. 110:4470; and Pauwels et al., (1986) Chemica Scripta 26:141-9), phosphorothioate (Mag et al., (1991) Nucleic Acids Res. 19:1437; and U.S. Pat. No. 5,644,048), phosphorodithioate (Briu et al., (1989) J. Am. Chem. Soc. 111:2321, O-methylphosphoroamidite linkages (see Eckstein, Oligonucleotides and Analogues: A Practical Approach, Oxford University Press), and peptide nucleic acid backbones and linkages (see Egholm, (1992) J. Am. Chem. Soc. 114:1895; Meier et al., (1992) Chem. Int. Ed. Engl. 31:1008; Nielsen, (1993) Nature, 365:566; Carlsson et al., (1996) Nature 380:207, all of which are incorporated by reference). Other analog nucleic acids include those with positive backbones (Denpcy et al., (1995) Proc. Natl. Acad. Sci. USA 92:6097; non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., (1988) J. Am. Chem. Soc. 110:4470; Letsinger et al., (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al., (1994) Bioorganic & Medicinal Chem. Lett. 4:395; Jeffs et al., (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., (1995) Chem. Soc. Rev. pp 169-1'76). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made. In some embodiments, peptide nucleic acids (PNA) which includes peptide nucleic acid analogs are used. These backbones are substantially non-ionic under neutral conditions, in contrast to the highly charged phosphodiester backbone of naturally occurring nucleic acids.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

In some embodiments, the binding element is a synthetic compound. Any numbers of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

Alternatively, some embodiments utilize natural compounds, as binding elements, in the form of bacterial, fungal, plant and animal extracts that are available or readily produced.

Additionally, natural or synthetically produced compounds are readily modified through conventional chemical, physical and biochemical means. Known pharmacological agents may be subjected to directed or random chemical modifications, including enzymatic modifications, to produce binding elements that may be used in the instant invention.

In some embodiment the binding element is a small organic compound. Binding elements can be synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or binding elements that can then be used in the present invention.

In some embodiments the binding element is a carbohydrate. As used herein the term carbohydrate is meant to include any compound with the general formula $(CH_2O)_n$. Examples of carbohydrates are di-, tri- and oligosaccharides, as well polysaccharides such as glycogen, cellulose, and starches.

In some embodiments the binding element is a lipid. As used herein the term lipid herein is meant to include any water insoluble organic molecule that is soluble in nonpolar organic solvents. Examples of lipids are steroids, such as cholesterol, and phospholipids such as sphingomyelin.

In some embodiments the binding element is a naturally occurring protein or fragment thereof. Examples of suitable proteins are integrins. Examples of suitable protein fragments are SH2 domains which have be used to detect phosphorylated protein epitopes (Dierck et al. Quantitative multiplexed profiling of cellular signaling networks using phosphotyrosine-specific DNA-tagged SH2 domains. Nat Methods (2006) vol. 3 (9) pp. 737-744).

In some embodiments the binding element is a MHC tetramer. As used herein, the term "MHC tetramer" is meant to include any compound with specific affinity for a particular T cell receptor (TCR). Generally, MHC tetramers consist of a streptavidin molecule conjugated to four biotinylated major histocompatibility complex (MHC) proteins, each carrying a peptide of a class recognized by a single TCR clonotype. An example of a MHC tetramer is the HLA-A2-Gag(77-85) tetramer which binds to the TCR of HIV-specific T cells (Altman et al. Phenotypic analysis of antigen-specific T lymphocytes. Science (1996) vol. 274 (5284) pp. 94-6).

Joining Elements

The term "Joining Element" includes a molecule (e.g., DNA, RNA, synthetic polymer, protein, peptide, peptide nucleic acids, RNA thiophosphates, leucine zippers, polymers, or peptide loops and other compounds that may perform the same function) which is capable of specifically binding (e.g. hybridizing for nucleic acids) to a region, e.g., a complementary joining molecule in the assembled detection complex. By "specifically bind" or "specifically hybridize" herein is meant that the partners bind with specificity sufficient to differentiate between the intended pair and other components or contaminants of the system. For example, it may be intended to join a specific binding element/labeling element pair and not another, different pair even though the different pair may have one of the elements in common. The specific joining occurs on the unit basis between the polymeric units. "Joining" is defined in the present invention to exclude stereospecific, antibody/antigen recognition sets. Examples of unit joining are the relationships between nucleic acids and other polymers that will join with one another by interacting on a unit-unit basis or via defined subgroups of units (e.g. the sequence A-B-C, wherein A, B, C can each be composed of 1 or more units) that interact with another 'complementary' group of cognate units (e.g. the sequence A'-B'-C', wherein each of A', B', and C' are composed of 1 or more units). The complementary pairs of units or groups composed of unit-sets will have sufficient affinity alone or in combination to allow for association of the joining elements to each other in a specific manner (see below).

Oligomer units can be defined as single molecule entities (such as nucleotides or amino acids), groups of such individual units composing a composite group unit, or high order polymers such as coiled coils or beta sheets. In addition, oligomers of one chemical type might be designed to bind oligomers of another chemical subunit nature. Chains of polypeptides or coiled coils might be designed to have specific affinity for chains of chemical units such as nucleotides that are composed of anything from 1 to 2 or more subunits.

A unit may be defined as any grouping of atoms that compose a recognizable entity that could be conceivably polymerized.

The binding should be sufficient to remain bound under the conditions of the assay, including wash steps to remove non-specific binding. In some embodiments, the dissociation constants of the pair will be less than about $10^{-4}$ to $10^{-9}$ $M^{-1}$, less than about $10^{-5}$ to $10^{-9}$ $M^{-1}$, or less than about $10^{-7}$ to $10^{-9}$ $M^{-1}$.

The term "cognate joining element" as used herein refers to either member of a pair of joining elements designed to specifically associate in a fully assembled detection complex.

In one embodiment of the disclosed invention, at least two joining elements facilitate the conjugation of the binding element to the labeling element and thus generate one assembled detection complex.

In another embodiment of the disclosed invention, each assembled detection complex is designed with an appropriate combination of joining elements such that a single class of binding elements is uniquely conjugated to a single class of labeling elements. An objective of uniquely conjugating one class of binding elements with one class of labeling elements is that measuring the presence of the labeling element will be a reliable surrogate for measuring the presence of the binding element, and thereby a reliable surrogate for measuring the presence of the target epitope.

Each joining element can be selected and optimized by empirical experimentation to have minimal binding to the other molecules present in the experiment, with the exception of the cognate joining element. For example, for a class of assembled detection complexes in which the joining elements are single-stranded DNA oligomers, the sequences of the joining elements may be selected to have minimal sequence complementarity to the genomic DNA that may be present in the experiment. Furthermore, in a multiplex experiment, the total pool of joining elements may be selected such that each joining element has minimal cross-complementarity to the other joining elements in the pool, with the exception of the cognate joining element. Detailed methods for selecting a pool of DNA oligomers tags with minimal complementarity to the other oligomers in the pool or to genomic DNA are detailed in U.S. Pat. No. 6,458,530. Automated systems and software may also be employed to analyze the cross hybridization potential of a large number of joining elements.

Figure 2:
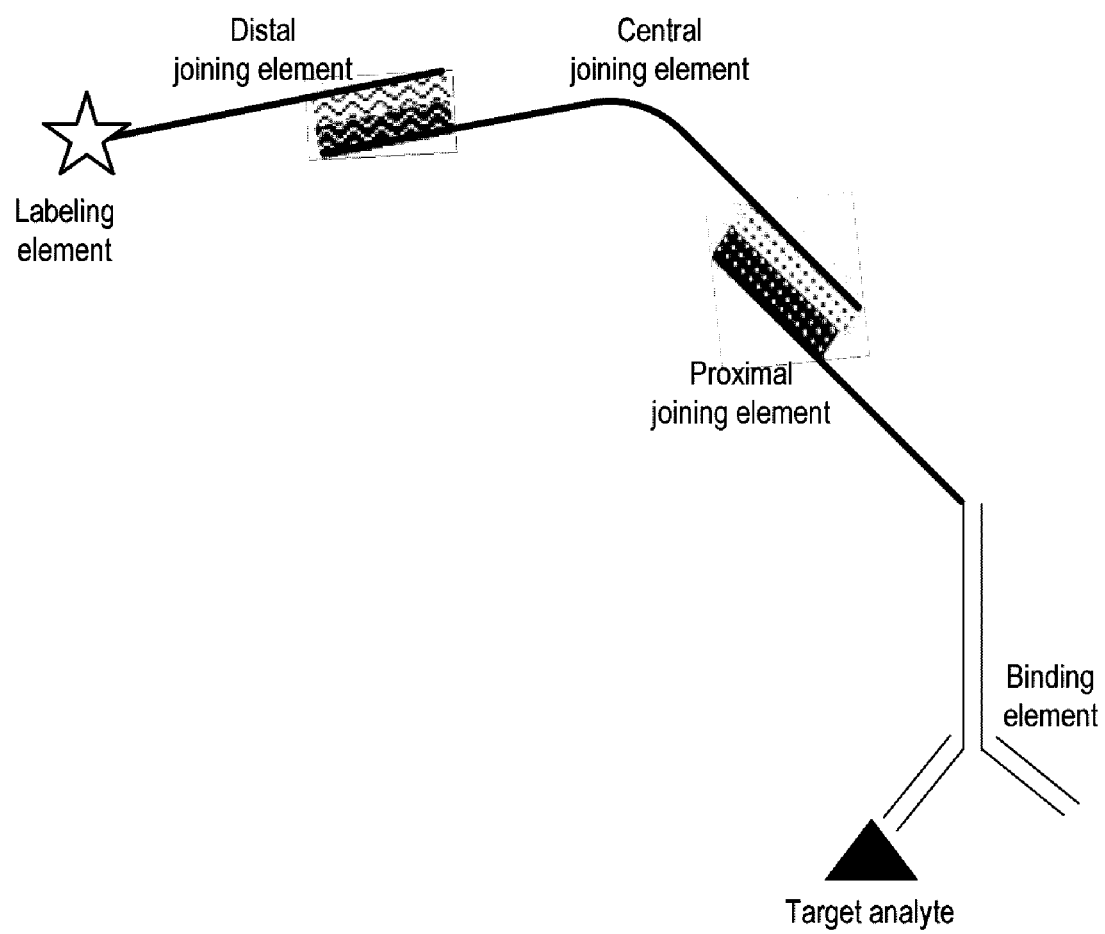
FIG. 2 shows the arrangement of one embodiment of the invention in which the binding element is joined to the labeling element through three joining elements.

In some embodiments three or more joining elements may be used to complete the conjugation of the binding element to the labeling element and thus generate one assembled detection complex. See FIG. 2.

In some embodiments many distinct classes of joining elements may be used simultaneously in a multiplex reaction generating many distinct classes of assembled detection complexes, wherein each class of assembled detection complexes is defined by the combination of binding element and labeling element present. In one embodiment, the binding elements and the labeling elements are joined after the binding element is contacted with its target. In other embodiments, the binding elements and the labeling elements are joined before the binding element is contacted with its target.

The joining element referred to herein as the "Proximal Joining Element" refers to the joining element nearest to the binding element (e.g., attached to the binding element) in the assembled detection complex.

In some embodiments, the proximal joining element is covalently attached to the binding element.

The joining element referred to herein as the "Distal Joining Element" refers to the joining element nearest to the labeling element (e.g., attached to the labeling element) in the assembled detection complex.

In some embodiments of the invention, the distal joining element is covalently attached to the labeling element.

The joining element referred to herein as the "Central Joining Element" refers to any joining element or elements that are part of the assembled detection complex, but are located between the distal joining element and the proximal joining element. Not all assembled detection complexes as contemplated by this patent will have or need a central joining element. An example of a central joining element is a joining element that binds (e.g., hybridizes for nucleic acids) to the distal joining element and the proximal joining element, thus bridging the labeling element and the binding element to generate the assembled detection complex. There may be 1, 2, 3, 4, 5, 6, 7, 8, 9, 10 or more central joining elements. For example, in the embodiments where there are more than one central elements, a first central element is bound to the proximal element, a second central element is bound to the distal element and the first and second central element are bound to each other directly or indirectly through one or more central elements.

In some embodiments, the joining element is a branched DNA molecule known in the art as a 'dendrimer', as described in Ong, K. K., Jenkins, A. L., Cheng, R., Tomalia, D. A., Durst, H. D., Jensen, J. L., Emanuel, P. A., Swim, C. R., and Yin, R. (2001) Dendrimer enhanced immunosensors for biological detection. Anal. Chim. Acta 444, 143-148. See also U.S. Pat. No. 6,806,047.

In some embodiments, the joining element is a phosphorothioate oligonucleotide. Phosphorothioate oligomers are more resistant to nuclease activity and can have higher binding affinities than their DNA or RNA counterparts. (Kurreck, Antisense technologies, Improvement through novel chemical modifications, Eur J Biochem (2003)). In some embodiments, the joining element is a RNA thiophosphates. In one embodiment, the joining element is a single-stranded DNA oligomer. In another embodiment, the joining element is a single-stranded RNA oligomer.

In some embodiments, the joining element is an oligomer of "locked nucleic acids", as described in Ng et al. Alternative nucleic acid analogues for programmable assembly: hybridization of LNA to PNA. Nano Lett (2005) vol. 5 (1) pp. 107-11.

In some embodiments, the joining element is an oligomer of left-helix DNA known as "L-DNA", as described in Hauser et al. Utilizing the left-helical conformation of L-DNA for analyzing different marker types on a single universal microarray platform. Nucleic Acids Res (2006) vol. 34 (18) pp. 5101-11.

In some embodiments, the joining element is a peptide with specific affinity for another class of joining elements. For example, "peptide nucleic acids" may be used as described in Ng et al. Alternative nucleic acid analogues for programmable assembly: hybridization of LNA to PNA. Nano Lett (2005) vol. 5 (1) pp. 107-11.

In some embodiments, the joining element is a protein with specific affinity for another class of joining elements. For example, a streptavidin joining element may be used to conjugate one or more biotin-labeled joining elements.

In some embodiments, the joining element is a linear polymer with specific affinity for another class of joining elements. For example, poly(N-vinylpyrrolidone) or poly(acrylic acid) polymers, as described in U.S. Pat. No. 5,686,071.

In some embodiments, the binding affinity of two cognate oligonucleotide joining elements is intentionally decreased by choosing oligonucleotide sequences that are less than 100% complementary.

A. Proximal Joining Element

In one embodiment, the proximal joining element is a single-stranded ribonucleic acid (RNA) or deoxyribonucleic acid (DNA) oligonucleotide or derivative thereof of length greater than 15 base pairs and covalently attached at its 3' terminus to the binding element. In some embodiments, the joining element is an oligonucleotide or a nucleic acid having more than 10, 12, 15, 17, 20, 25, 30, 35, 40, 45, 50, 75, 85 or 100 or more bases in length. In some embodiments the joining element is an oligonucleotide or a nucleic acid having about 15 to about 40 bases in length. In some embodiments, the joining element is an oligonucleotide or a nucleic acid having about 15 to about 30 bases in length. In some embodiments, the joining element is an oligonucleotide or a nucleic acid having about 15 to about 25 bases in length.

It is desirable that the proximal joining element does not interfere with the affinity or specificity for the target analyte of the binding element to which it is conjugated. It is known that DNA oligos up to 300 by in length can be conjugated to antibodies without interfering with antibody binding. (Niemeyer et al. Immuno-PCR: high sensitivity detection of proteins by nucleic acid amplification. Trends in Biotechnology (2005) vol. 23 (4) pp. 208-216)

In some embodiments the proximal joining element may be capable of specifically hybridizing to a complementary region in two or more distal joining elements of the same class, simultaneously or sequentially. In some embodiments a proximal joining element may be capable of specifically hybridizing to two or more central joining elements of the same class, simultaneously.

Figure 3:
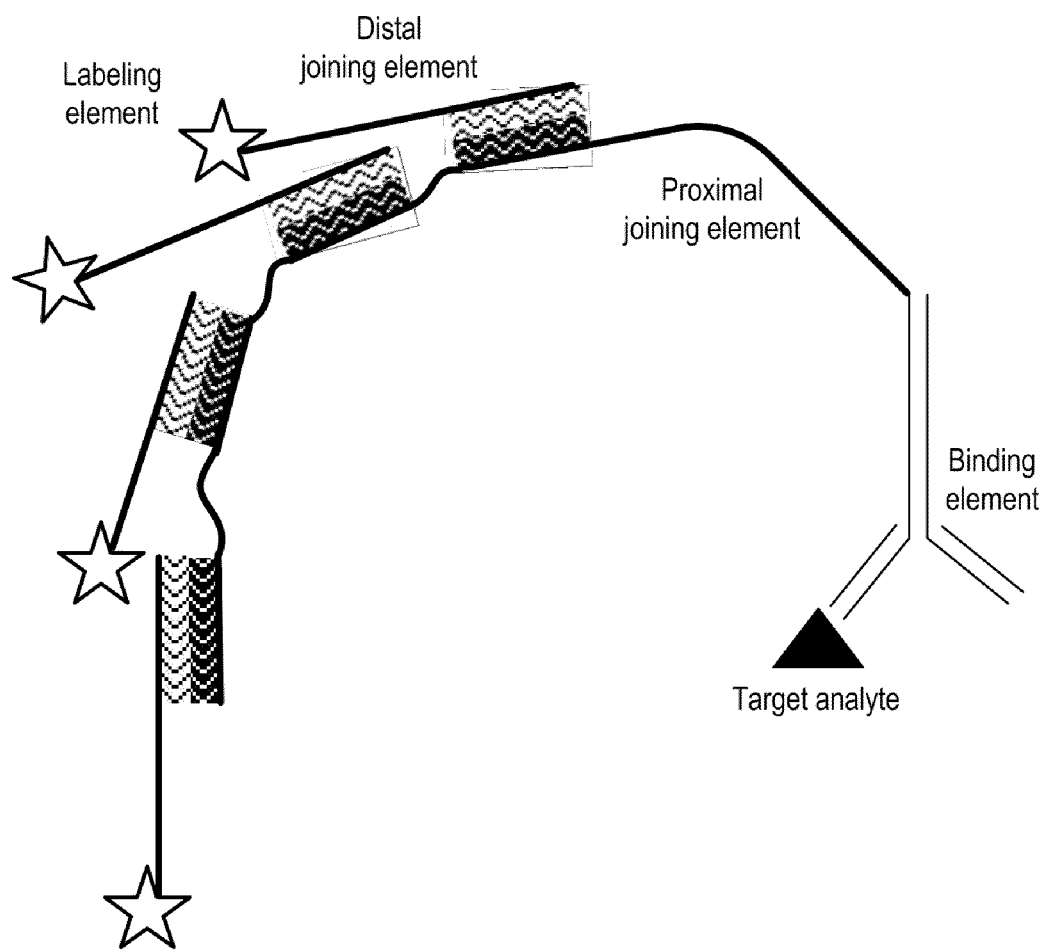
FIG. 3 shows the arrangement of one embodiment of the invention in which the binding element is joined to a plurality of labeling elements through a single proximal joining element joined to a plurality of distal joining elements.

An objective of binding multiple joining elements with a single proximal joining element can be to increase the number of labels bound to a given analyte, thereby enhancing the sensitivity of the assay (See FIG. 3).

Figure 4:
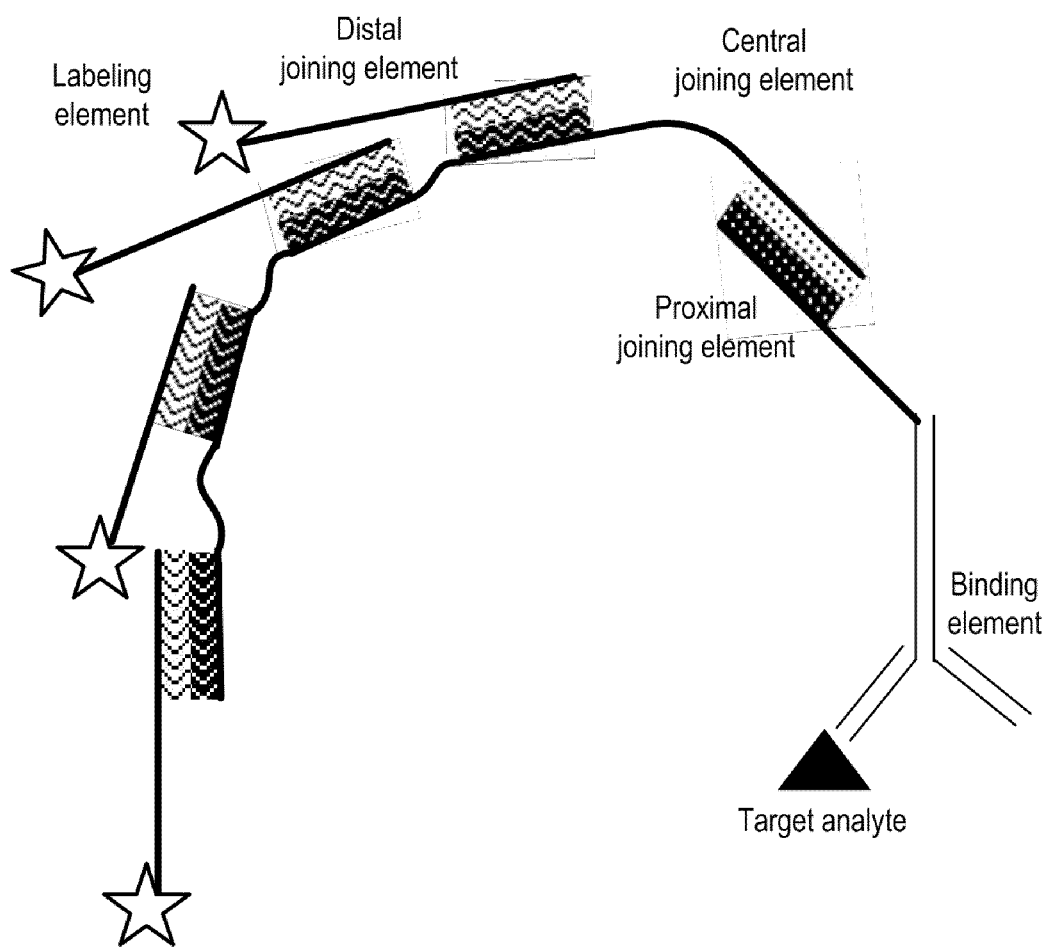
FIG. 4 shows the arrangement of one embodiment of the invention in which the binding element is joined to a plurality of labeling elements through a single proximal joining element joined to a single central joining element that is joined to a plurality of distal joining elements.

In some embodiments, a proximal joining element is capable of specifically hybridizing to a central joining element that is capable of specifically hybridizing to a complementary region in two or more distal joining elements of the same class, simultaneously or sequentially (See FIG. 4).

In some embodiments, the proximal joining element is a substrate for rolling circle amplification. In some embodiments, the proximal joining element is a loop of DNA that is a substrate for rolling circle amplification, attached to the binding element by means of a linear polymer 'tether' such that the product of rolling circle amplification remains topologically locked to the binding element, as described in U.S. Pat. No. 5,854,033.

In some embodiments, the proximal joining element is a dendrimer having one branch covalently attached to the binding element and having a plurality of free branches with identical specificity for a single class of central or distal joining elements.

B. Distal Joining Element

In one embodiment, the distal joining element is a single-stranded ribonucleic acid (RNA) or deoxyribonucleic acid (DNA) oligonucleotide or derivative thereof of length greater than 15 base pairs and covalently attached at its 5' terminus to the binding element. In some embodiments, the joining element is an oligonucleotide or a nucleic acid having more than 10, 12, 15, 17, 20, 25, 30, 35, 40, 45, 50, 75, 85 or 100 bases in length. In some embodiments, the joining element is an oligonucleotide or a nucleic acid having about 15 to about 40 bases in length. In some embodiments, the joining element is an oligonucleotide or a nucleic acid having about 15 to about 30 bases in length. In some embodiments, the joining element is an oligonucleotide or a nucleic acid having about 15 to about 25 bases in length.

It is desirable that the distal joining element does not interfere with the detection of the labeling element. For example, in an embodiment in which the labeling element is an enzyme, the distal joining element must be conjugated to the enzyme at an amino acid residue that does not affect the activity of the enzyme.

C. Central Joining Element

In some embodiments, the assembled detection complex contains one or more central joining elements that connect the binding element to the labeling element.

In some embodiments, the central joining element is a single-stranded deoxyribonucleic acid (DNA) oligonucleotide of length greater than 30 base pairs, having at least 15 base pairs at the 3' end that are greater than 86%, 88%, 90%, 92%, 94%, 96%, 98% or 100% complementary to the proximal joining element, and optionally having at least 15 base pairs at the 5' end that are 100% complementary to the distal joining element. Oligonucleotide central joining elements have been used in other systems, such as that described in U.S. Pat. No. 6,261,771, which is hereby incorporated by reference in its entirety.

In some embodiments, the central joining element is a dendrimeric DNA molecule with one branch complementary to the proximal joining element and a plurality of free oligomers complementary to the distal joining element. An objective of using a dendrimeric molecule in this capacity is to amplify the signal produced by each binding element by attaching multiple labeling elements per binding element. See also U.S. Pat. No. 6,806,047.

An objective of including a central joining element in the assembled detection complex is that the manufacturer of the assembled detection complexes can efficiently synthesize many different classes of central joining elements, and is thereby not obligated to conjugate every labeling element to every distal joining element, nor every binding element to every proximal joining element.

Labeling Element

The methods and compositions of the instant invention provide elements comprising a label or tag, referred to herein as the "Labeling Element". By label is meant a molecule that can be directly (i.e., a primary label) or indirectly (i.e., a secondary label) detected; for example a label can be visualized and/or measured or otherwise identified so that its presence or absence can be known. A compound can be directly or indirectly conjugated to a label which provides a detectable signal, e.g. radioisotopes, fluorophores, enzymes, antibodies, particles such as magnetic particles, chemiluminescent molecules, or specific binding molecules, etc. Specific binding molecules include pairs, such as biotin and streptavidin, digoxigenin and anti-digoxigenin etc. Examples of labels include, but are not limited to, optical fluorescent and chromogenic dyes including labels, label enzymes and radioisotopes.

In some embodiments, one or more classes of assembled detection complexes are uniquely labeled. Using the example of two different assembled detection complexes, A and B, by "uniquely labeled" is meant that in assembled detection complex A, the labeling element is a first label, and in assembled detection complex B, the labeling element is a second label, wherein the first and second labels are detectable and distinguishable, making the first assembled detection complex and the second assembled detection complex uniquely labeled.

In general, labels fall into four classes: a) isotopic labels, which may be radioactive or heavy isotopes; b) magnetic, electrical, thermal labels; c) colored, optical labels including luminescent, phosphorous and fluorescent dyes or moieties; and d) binding partners. Labels can also include enzymes (horseradish peroxidase, luciferase, etc.) and magnetic particles. In some embodiments, the detection label is a primary label. A primary label is one that can be directly detected, such as a fluorophore.

Labels include optical labels such as fluorescent dyes or moieties. Fluorophores can be either "small molecule" fluors, or proteinaceous fluors (e.g. green fluorescent proteins and all variants thereof).

Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference.

Suitable fluorescent labels also include, but are not limited to, green fluorescent protein (GFP; Chalfie, et al., Science 263 (5148):802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12): 5408-5417 (1993)), .beta.-galactosidase (Nolan, et al., Proc Natl Acad Sci USA 85(8):2603-2607 (April 1988)) and Renilla WO 92/15673; WO 95/07463; WO 98/14605; WO 98/26277; WO 99/49019; U.S. Pat. Nos. 5,292,658; 5,418,155; 5,683,888; 5,741,668; 5,777,079; 5,804,387; 5,874,304; 5,876,995; and 5,925,558). All of the above-cited references are expressly incorporated herein by reference.

In some embodiments, labels for use in the present invention include: Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes) (Eugene, Oreg.), FITC, Rhodamine, and Texas Red (Pierce, Rockford, Ill.), Cy5, Cy5.5, Cy7 (Amersham Life Science, Pittsburgh, Pa.). Tandem conjugate protocols for Cy5PE, Cy5.5PE, Cy7PE, Cy5.5APC, Cy7APC are known in the art. Quantitation of fluorescent probe conjugation may be assessed to determine degree of labeling and protocols including dye spectral properties are also well known in the art. In some embodiments the fluorescent label is conjugated to an aminodextran linker which is conjugated to a binding element or antibody. Additional labels listed in and are available through the on-line and hard copy catalogues of BD Biosciences, Beckman Coulter, AnaSpec, Invitrogen, Cell Signaling Technology, Millipore, eBioscience, Caltag, Santa Cruz Biotech, Abcam and Sigma, the contents of which are incorporated herein by reference.

In some embodiments, the fluorescent label is a GFP and, more preferably, a *Renilla, Ptilosarcus*, or *Aequorea* species of GFP.

In some embodiments, the secondary label is a chemically modifiable moiety. In this embodiment, labels comprising reactive functional groups are incorporated into the molecule to be labeled. The functional group can then be subsequently labeled (e.g. either before or after the assay) with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference).

In some embodiments, multiple fluorescent labels are employed in the methods and compositions of the present invention. In some embodiments, each label is distinct and distinguishable from other labels.

As will be appreciated in the art antibody-label conjugation may be performed using standard procedures or by using protein-protein/protein-dye cross-linking kits from Molecular Probes (Eugene, Oreg.).

In some embodiments, labeling elements are comprised of quantum dots as disclosed by Chattopadhyay, P. K. et al. Quantum dot semiconductor nanocrystals for immunophenotyping by polychromatic flow cytometry. Nat. Med. 12, 972-977 (2006). Quantum dot labels are commercially available through Invitrogen, http://probes.invitrogen.com/products.q-dot/.

Quantum dot labeled antibodies can be used alone or they can be employed in conjunction with organic fluorochrome-conjugated antibodies to increase the total number of labels available. (Invitrogen, Carlsbad, Calif.). As the number of labeled antibodies increase so does the ability for subtyping known cell populations. Additionally, labeling elements may be comprised of chelated or caged lanthanides as disclosed by Erkki, J. et al. Lanthanide chelates as new fluorochrome labels for cytochemistry. J. Histochemistry Cytochemistry, 36:1449-1451, 1988, and U.S. Pat. No. 7,018,850, entitled Salicylamide-Lanthanide Complexes for Use as Luminescent Markers. Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remade et al., Proc. Natl. Sci. USA (2000) 18:553-8, each expressly incorporated herein by reference) as well as confocal microscopy.

In some embodiments, the labeling elements are comprised of isotope tags suitable for Inductively Coupled Plasma Mass Spectrometer (ICP-MS) as disclosed in Tanner et al. Spectrochimica Acta Part B: Atomic Spectroscopy, 2007 March; 62(3):188-195; Ornatsky et al, mRNA Detection in Leukemia Cell lines by Novel Metal-Tagged in situ Hybridization using Inductively Coupled Plasma Mass Spectometry, Translational Oncogenomics (2006):1, 1-9; Ornatsky et al, Multiple Cellular Antigen Detection by ICP-MS, J. Imm. Methods 308 (2006) 68-76; and Lou et al., Polymer-Based Elemental Tags for Sensitive Bioassays, Angew. Chem. Int. Ed., (2007) 46, 6111-6114.

In some embodiments, the labeling elements are comprised of radiodense tags (e.g. gold particles). In some embodiments, the labeling elements are comprised of electron-dense tags (e.g. gold particles). In some embodiments, the labeling elements are comprised of radioactive isotopes (e.g. $^{111}$Indium) as disclosed in U.S. Pat. No. 4,421,735. In some embodiments, the labeling elements are comprised of paramagnetic particles (e.g. iron oxide-impregnated beads) as disclosed in U.S. Pat. Nos. 5,385,707, 6,020,210, and 6,576,428. In some embodiments, the labeling elements are comprised of agarose particles suitable for purification by centrifugation or column elution. In some embodiments, the labeling elements are comprised of mass tags (e.g., e-tags), such as those disclosed in United States Patent Application 2003/0207300. In some embodiments, the labeling elements are comprised of nanoparticles suitable for detection by surface enhanced or Raman spectroscopy, such as those disclosed in U.S. Pat. No. 6,514,767. In some embodiments, the labeling elements are comprised of vesicle tags, such as those disclosed in United States Patent Application 2007/0172827.

Activatable Elements

The methods and compositions of the invention may be employed to detect and/or quantitate any activatable element in a cellular pathway, or collections of such activatable elements. A plurality of activatable elements in a single or multiple distinct pathways may be detected and/or quantitated (sequentially or simultaneously), or subsets of activatable elements within a single pathway or across multiple pathways may be detected and/or quantitated (again, sequentially or simultaneously).

In some embodiments, the activation state of an activatable element is determined. The activation state of an individual activatable element is either in the on or off state. As an illustrative example, and without intending to be limited to any theory, an individual phosphorylatable site on a protein will either be phosphorylated and then be in the "on" state or it will not be phosphorylated and hence, it will be in the "off" state. See Blume-Jensen and Hunter, Nature, vol 411, 17 May 2001, p 355-365. The terms "on" and "off" when applied to an activatable element that is a part of a cellular constituent, are used here to describe the state of the activatable element (e.g., phosphorylated is "on" and non-phosphorylated is "off"), and not the overall state of the cellular constituent of which it is a part. Typically, a cell possesses a plurality of a particular protein or other constituent with a particular activatable element and this plurality of proteins or constituents usually has some proteins or constituents whose individual activatable element is in the on state and other proteins or constituents whose individual activatable element is in the off state. When the activation state of an activatable element is measured, it can be measured through the use of a binding element that recognizes a specific activation state, only those activatable elements in the specific activation state recognized by the binding element, representing some fraction of the total number of activatable elements, will be bound by the binding element to generate a measurable signal. In some embodiments, an increased in expression of an activatable element is indicative of the activation state of the activatable element. Thus, the activation state can be measured by measuring the expression of the activatable element. The measurable signal corresponding to the summation of individual activatable elements of a particular type that are activated in a single cell is the "activation level" for that activatable element in that cell.

In some embodiments, the activation level of an activatable element is determined. Activation levels for a particular activatable element may vary among individual cells so that when a plurality of cells is analyzed, the activation levels follow a distribution. The distribution may be a normal distribution, also known as a Gaussian distribution, or it may be of another type. Different populations of cells may have different distributions of activation levels that can then serve to distinguish between the populations.

In some embodiments, the basis determining the activation levels of one or more activatable elements in cells may use the distribution of activation levels for one or more specific activatable elements which will differ among different phenotypes. A certain activation level, or more typically a range of activation levels for one or more activatable elements seen in a cell or a population of cells, is indicative that that cell or population of cells belongs to a distinctive phenotype. Other measurements, such as cellular levels (e.g., expression levels) of biomolecules that may not contain activatable elements, may also be used in addition to activation levels of activatable elements; it will be appreciated that these levels also will follow a distribution, similar to activatable elements. Thus, the activation level or levels of one or more activatable elements, optionally in conjunction with levels of one or more levels of biomolecules that may not contain activatable elements, of one or more cells in a population of cells may be used in the methods described herein.

Activatable elements can be intracellular biomolecules or extracellular biomolecules, e.g., proteins, RNA, DNA, carbohydrates, lipid and metabolites.

In some embodiments, the invention provides for the detection and/or quantitation of a plurality of intracellular activatable elements. The term "plurality" as used herein refers to two or more. In some embodiments, at least about 2, 3, 4, 5, 6, 7, 8, 9, 10, or more than 10 activatable elements are detected and/or quantitated.

In some embodiments, the activatable element is a protein. Examples of proteins that may include activatable elements include, but are not limited to kinases, phosphatases, lipid signaling molecules, adaptor/scaffold proteins, cytokines, cytokine regulators, ubiquitination enzymes, adhesion molecules, cytoskeletal/contractile proteins, heterotrimeric G proteins, small molecular weight GTPases, guanine nucleotide exchange factors, GTPase activating proteins, caspases, proteins involved in apoptosis, cell cycle regulators, molecular chaperones, metabolic enzymes, vesicular transport proteins, hydroxylases, isomerases, deacetylases, methylases, demethylases, tumor suppressor genes, proteases, ion channels, molecular transporters, transcription factors/DNA binding factors, regulators of transcription, and regulators of translation.

Examples of activatable elements, activation states and methods of determining the activation level of activatable elements are described in U.S. Pat. Nos. 7,381,535; 7,393, 656; 7,563,584 and U.S. Pat. Ser. Nos. 10/193,462; 11/655, 785; 11/655,789; 11/655,821; 11/338,957; 12/432,720; 12/229,476; 12/432,239; 12/460,029; 12/471,158; 61/216, 825; 61/162,673; 61/157,900; 61/151,387; 61/104,666; 61/226,878; 61/218,718; 61/182,518; 61/170,348; 61/144, 684; 61/113,823; 61/181,211; 61/162,598; 61/108,803; 61/182,638; 61/177,935; 61/155,373; 12/293,081; 61/186, 619; 61/156,754; 61/106,462; 61/176,420; 12/538,643; 12/501,274; 61/079,537; 12/501,295; 61/146,276; and 61/144,955, incorporated herein by reference.

In some embodiments, the protein that may be activated is selected from the group consisting of HER receptors, PDGF receptors, FLT3 receptor, Kit receptor, FGF receptors, Eph receptors, Trk receptors, IGF receptors, Insulin receptor, Met receptor, Ret, VEGF receptors, erythropoietin receptor, thromobopoetin receptor, CD114, CD116, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tp1, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PP5, inositol phosphatases, PTEN, SHIPs, myotubularins, phosphoinositide kinases, phopsholipases, prostaglandin synthases, 5-lipoxygenase, sphingosine kinases, sphingomyelinases, adaptor/ scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon γ, interferon α, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/ KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases, Caspase 2, Caspase 3, Caspase 6, Caspase 7, Caspase 8, Caspase 9, Bcl-2, Mcl-1, Bcl-XL, Bcl-w, Bcl-B, Al, Bax, Bak, Bok, Bik, Bad, Bid, Bim, Bmf, Hrk, Noxa, Puma, IAPs, XIAP, Smac, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, caveolins, endosomal sorting complex required for transport (ES-CRT) proteins, vesicular protein sorting (Vsps), hydroxylases, prolyl-hydroxylases PHD-1, 2 and 3, asparagine hydroxylase FIH transferases, Pin1 prolyl isomerase, topoisomerases, deacetylases, Histone deacetylases, sirtuins, histone acetylases, CBP/P300 family, MYST family, ATF2, DNA methyl transferases, Histone H3K4 demethylases, H3K27, JHDM2A, UTX, VHL, WT-1, p53, Hdm, PTEN, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Gycoprotein, nucleoside transporters, Ets, Elk, SMADs, Rel-A (p65-NFKB), CREB, NFAT, ATF-2, AFT, Myc, Fos, Spl, Egr-1, T-bet, β-catenin, HIFs, FOXOs, E2Fs, SRFs, TCFs, Egr-1, β-catenin, FOXO STAT1, STAT 3, STAT 4, STAT 5, STAT 6, p53, WT-1, HMGA, pS6, 4EPB-1, eIF4E-binding protein, RNA polymerase, initiation factors, elongation factors.

In some embodiments, the activatable element is a phosphoprotein.

Methods

In some embodiments, the invention provides methods, including methods to detect and/or quantify the abundance of an analyte in a sample, in situ. In some embodiments, the invention provides methods, including methods to detect and/ or quantify multiple analytes in a complex sample simultaneously, in situ. The information can be used in any application where in situ measurement is desirable, including flow cytometry, immunofluorescence, histology, array-based and dot-blot or slot-blot ELISA platforms. The information obtained from such applications may be useful in compound screening for drug development purposes, prognosis and diagnosis, including susceptibility to disease(s), status of a diseased state and response to changes in the environment, such as the passage of time, treatment with drugs or other modalities. Through the use of activation state-specific binding elements, such as phospho-specific antibodies, the physiological status of the cells in a sample (e.g. clinical sample) may be classified according to the activation of cellular pathways of interest, or according to their ability to respond to therapeutic agents and treatments. See the following United States patents and applications for examples of this technology: U.S. Pat. Nos. 7,381,535 and 7,393,656 and U.S. Ser. Nos. 10/193,462; 11/655,785; 11/655,789; 11/655,821; 11/338,957, 61/048,886; 61/048,920; 61/048,657; 61/079,766, and 61/085,789.

1. Selection of Samples for an Assay

One or more cells, or samples containing one or more cells, can be isolated from body samples, such as, but not limited to, smears, sputum, biopsies, secretions, cerebrospinal fluid, bile, blood, lymph fluid, urine and feces, a lavage of a tissue or organ (e.g. lung) or tissue which has been removed from organs, such as breast, lung, intestine, skin, cervix, prostate, and stomach. For example, a tissue sample can comprise a region of functionally related cells or adjacent cells. Such samples can comprise complex populations of cells, which can be assayed as a population, or separated into sub-populations. Such cellular and acellular samples can be separated by centrifugation, elutriation, density gradient separation, apheresis, affinity selection, panning, FACS, centrifugation with Hypaque, etc. By using antibodies specific for markers identified with particular cell types, a relatively homogeneous population of cells may be obtained. Alternatively, a heterogeneous cell population can be used. Cells can also be separated by using filters. For example, whole blood can also be applied to filters that are engineered to contain pore sizes that select for the desired cell type or class. Rare pathogenic cells can be filtered out of diluted, whole blood following the lysis of red blood cells by using filters with pore sizes between 5 to 10 μm, as disclosed in U.S. patent application Ser. No. 09/790,673. Other devices can separate tumor cells from the bloodstream, see Demirci U, Toner M., Direct etch method for microfluidic channel and nanoheight post-fabrication by picoliter droplets, Applied Physics Letters 2006; 88 (5), 053117; and Irimia D, Geba D, Toner M., Universal microfluidic gradient generator, Analytical Chemistry 2006; 78: 3472-3477. Once a sample is obtained, it can be used directly, frozen, or maintained in appropriate culture medium for short periods of time. Methods to isolate one or more cells for use according to the methods of this invention are performed according to standard techniques and protocols well-established in the art.

Suitable cells include those cell types associated in a wide variety of disease conditions, even while in a non-diseased state. Accordingly, suitable eukaryotic cell types include, but are not limited to, tumor cells of all types (e.g. melanoma, myeloid leukemia, carcinomas of the lung, breast, ovaries, colon, kidney, prostate, pancreas and testes), cardiomyocytes, dendritic cells, endothelial cells, epithelial cells, lymphocytes (T-cell and B cell), mast cells, eosinophils, vascular intimal cells, macrophages, natural killer cells, erythrocytes, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include primary disease state cells, such as primary tumor cells. Suitable cells also include known research cells, including, but not limited to, Jurkat T cells, NIH3T3 cells, CHO, COS, etc. See the ATCC cell line catalog, hereby expressly incorporated by reference.

In some embodiments, the cells are cultured post collection in a media suitable for revealing the target analyte (e.g. RPMI, DMEM) in the presence, or absence, of serum such as fetal bovine serum, bovine serum, human serum, porcine serum, horse serum, or goat serum. When serum is present in the media it could be present at a level ranging from 0.0001% to 100%. In some embodiments serum is present in the media at a level ranging from 0.0001% to 90%. In some embodiments serum is present in the media at a level ranging from 0.01% to 30%. In some embodiments serum is present in the media at 1, 2, 3, 4, 5, 6, 7, 8, 9 or 10%. In some embodiments, serum is present in the media at any suitable level.

In some embodiments, the cell is a hematopoietic cell. Examples of hematopoietic cells include but are not limited to pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells.

In some embodiments, the cells used in the present invention are taken from a patient. Cells used in the present invention can be purified from whole blood by any suitable method.

2. Selection of Compatible Elements for an Assay

As used herein, the phrase "experimental design" and grammatical equivalents thereof refer to the samples, conditions (e.g. physiological perturbations, time points), and target analytes selected for inclusion in an experiment. As will be appreciated by those in the art, experimental design is generally influenced by the biological system at hand and the research question under study.

As used herein, the phrase "detection complex design" and grammatical equivalents thereof refer to the binding elements, joining elements, and labeling elements selected for use in an assay. Detection complex design is generally influenced by the cost and availability of reagents, as well as the compatibility of different reagents within the system. In multiplex assays, the abundance of multiple analytes can be measured simultaneously because each class of analyte is labeled by a different class of detectable label, and all classes of detectable labels can be measured simultaneously. In a well-designed multiplex assay, the signal of each class of label is a faithful representation of the abundance of each class of analyte in the sample.

In one embodiment of the invention, detection complexes intended for use in multiplex assays must be designed such that each class of labeling element conjugates specifically to one class of binding element, and each class of binding element binds specifically to one class of target analyte.

In some embodiments, detection complex design comprises: Calculating the binding affinity of all possible combinations of joining elements in the assay; selecting a pool of cognate joining element pairs wherein each joining element has maximal affinity for its cognate joining element and minimal off-target affinity for the other joining elements in the assay; selecting a pool of labeling elements with minimal interference and suitable for simultaneous measurement on the available detection instrument.

In some embodiments, detection complex design may be facilitated by a software program that predicts the binding affinity of all possible joining elements in the assay, and automatically selects a pool of compatible joining elements for an assay.

In some embodiments, multiple classes of compatible binding elements may be selected for inclusion in a kit comprising: Multiple classes of labeling elements pre-conjugated to distal joining elements; multiple classes of binding elements pre-conjugated to proximal joining elements; multiple classes of central joining elements wherein each class of joining element is designed to specifically conjugate one distal joining element and one proximal joining element in the kit; software to assist the user in choosing an appropriate set of elements to label the analytes in their experiment using the available detection instrument; and instructions for use.

For example, in one embodiment, the kit comprises a binding element; a first joining element attached to each binding element in a conformation that allows binding to another binding element; a labeling element; a second joining element attached to the labeling element in a conformation that allows binding to another joining element; wherein the first and second joining elements are capable of directly or indirectly binding under the appropriate conditions; and instructions to select a binding element and a labeling element to be attached. Kits in alternative embodiments may include more than 1, 2, 3, 4, 5, 6 or more joining elements per pair of binding and labeling elements. Other components of the kit are consistent with previously recited elements noted above, such as types of labels or binding elements.

In some embodiments, there are more than 5, 6, 7, 8, 9, 10, 15, 17, 20, 25, 30, 35, 40, 45, 50, 55, 60, 65, 70, 75, 80, 85, 90, 100, 125, 150, 175, 200, 250, 300, 350, 400, 500, 750, 1000 or more possible combinations of binding element and labeling element in the set of reagents. The use of joining elements of the present invention allows for a greater number of combinations of binding and labeling elements than other methods. A combination such as this may be included in one or more kits.

3. Synthesis of Detection Complex Components

As used herein, the phrase "detection complex component" and grammatical equivalents thereof refer to any element or conjugation of elements that require no further assembly or modification before use in a self-assembly reaction. Examples of detection complex components include: A central binding joining element; a binding element covalently linked to a proximal joining element; a labeling element covalently linked to a distal joining element.

In some embodiments, synthesis of a detection complex component entails conjugating a single-stranded DNA oligonucleotide to a protein, such as an antibody. Methods for covalently linking a protein and an oligonucleotide are described in Zubin, E. M., Romanova, E. A., and Oretskaya, T. S. (2002) Modern methods for the synthesis of peptide-oligonucleotide conjugates. *Russ. Chem. Rev.* 71, 239-264. In some embodiments, a detection complex component is synthesized by modifying the oligonucleotide to include a thiopyridyl disulfide and reacting with a protein in reducing conditions such that the thiopyridyl disulfide and a reactive cysteine on the protein form a disulfide bond. In some embodiments, a detection complex component is synthesized by modifying the protein with a hydrazide group and modifying the oligonucleotide to include an aldehyde group, then combining them to form a hydrazone bond. In some embodiments, a detection complex component is synthesized by reacting the oligonucleotide and the protein with a homobifunctional linker such as bis(sulfosuccinimidyl)suberate (BS). In some embodiments, a detection complex component is synthesized by reacting the oligonucleotide and the protein a heterobifunctional crosslinker such as succinimidyl 4-[Nmaleimidomethyl]-cyclohexane-1-carboxylate (SMCC), N-[γ-maleimidobutyryloxy]succinimide ester (GMBS), succinimidyl 4-hydrazinonicotinate acetone hydrazone (SANH), succinimidyl 4[p-maleimidophenyl]-butyrate (SMPB), or derivatives thereof, such as sulfo-SMCC or sulfo-SMPB. These crosslinking agents take advantage of functional amino or thiol groups either on the oligonucleotide or protein to form a covalent link, as described in Tang et al. DNA-directed assembly of protein microarrays. Front Biosci (2008) vol. 13 pp. 5755-71. In some embodiments, a detection complex component is synthesized by conjugating an aminated oligonucleotide to a protein using SATA chemistry as described by Hendrickson et al. (1995).

4. Assembly of Detection Complexes and Labeling of Target Analyte

In some embodiments, the invention provides methods, including methods of self-assembly of detection complex components in a simplex or multiplex reaction yielding assembled detection complexes. The user must optimize the timing and conditions of each step in the assembly procedure for each class of assay. For example, if the self-assembly of joining elements performs best in a buffer with high concentration of salt, but the binding of the binding element to the target analyte is strongest in a buffer with low concentration of salt, the user may choose to perform the joining element self-assembly operation before the target binding operation.

(i) Timing

In some embodiments, the joining element self-assembly operation is performed before the target binding operation. In some embodiments, the joining element self-assembly operation is performed after the target binding operation. In some embodiments involving more than one class of fully assembled detection complexes, the joining element self-assembly operation is performed for a subset of detection complexes before the target binding operation, while the joining element self-assembly operation is performed for the remaining detection complexes after the target-binding operation.

(ii) Joining Element Self-Assembly Operation

The optimal conditions for self-assembly of cognate joining elements depend on the type of joining elements and the stability of other elements in the assay, such as the target analyte. For example, if the joining element self-assembly operation is to be performed during or after the target binding operation, a buffer must be used that preserves the binding activity of the binding element and all joining elements until the binding conjugation operations are complete. Furthermore, as will be appreciated by those in the art, the specificity and sensitivity of the binding reactions may be adjusted by altering the composition of the buffer system and adjusting the molar ratios of each element in the system.

In some embodiments, detection complex components having cognate joining elements comprised of single-stranded DNA with 100% sequence complementarity may be combined in equal molar concentrations in an aqueous buffer comprising 1 M NaCl, 10 mM Tris-HCl, 1 mM EDTA and 0.01% SDS, and allowed to self-assemble for two hours at room temperature.

In some embodiments, detection complex components may be combined in a high-salt buffer. An objective of increasing the ionic strength of the buffer is to increase the stringency of the self-assembly reaction between joining elements, and thereby reduce non-specific binding.

In some embodiments, detection complex components may be combined with one detection complex component in molar excess of the other. An objective of increasing the molar ratio of the detection complex components is to saturate the self-assembly reaction between detection complex components, especially when the binding element is less abundant in the system.

In some embodiments, detection complex components may be combined at temperatures greater than 2° C., 4° C., 22° C., 37° C., 42° C., or 65° C. An objective of increasing the temperature of the reaction is to increase the stringency of the self-assembly reaction between joining elements, and thereby reduce non-specific binding. In some embodiments, detection complex components may be combined at temperatures of about 35° C. to about 42° C. In some embodiments, detection complex components may be combined at temperatures of about 37° C.

In some embodiments, oligonucleotide joining elements which remain unbound at the completion of the self-assembly reaction may be digested by the addition of a purified exonuclease enzyme with specificity for single-stranded nucleic acids. For example, nuclease Si may be used to digest single-stranded DNA oligomers. It is desirable that the user optimizes conditions of the exonuclease digestion procedure to avoid nonspecific digestion of double-stranded oligomer complexes.

In some embodiments, a rolling circle amplification step may be used to amplify a proximal joining element prior in situ to the self-assembly reaction, as disclosed in U.S. Pat. No. 5,854,033. An objective of amplifying the proximal joining element in situ is to increase the number of binding sites for distal joining elements, thereby increasing the number of labeling elements conjugated to each binding element, and enhancing the sensitivity of the assay, while maintaining the molecular localization of the labeling element to the target analyte.

In some embodiments, the self-assembly reaction may be performed using a plurality of classes of central joining elements to form a plurality of classes of assembled detection complexes. An objective of performing multiplex self-assembly operations using a central joining element is to increase the diversity of assays that can be performed by reusing a core set of detection complex components.

In some embodiments, a step of the self-assembly reaction is to covalently ligate cognate oligonucleotide joining elements in a double-stranded conformation using an enzyme, such as DNA ligase. An objective of ligating cognate joining elements is to complement the ionic bonds of the binding interaction with covalent bonds, thereby reducing the possibility of dissociation.

In some embodiments, a step of the self-assembly reaction is to covalently crosslink cognate joining elements using a chemical crosslinking reagent, such as formaldehyde. An objective of ligating cognate joining elements is to complement the ionic bonds of the binding interaction with covalent bonds, thereby reducing the possibility of dissociation.

In some embodiments in which the self-assembly reaction precedes the target binding operation, the assembled detection complexes may be purified to remove excess or unbound detection complex components. In some embodiments, purification of assembled detection complexes is achieved using a size exclusion column, such as a Sephadex column. In some embodiments, purification of assembled detection complexes is achieved using an affinity column, such as a column containing agarose beads coupled to joining elements complementary to those used in the assembled detection complexes. An objective of purifying the assembled detection complexes is to remove free detection complex components that may bind to other contaminants in the assay, such as genomic DNA.

(iii) Target Binding Operation

As used herein, the phrase "target binding" and grammatical equivalents thereof refer to the act of contacting a binding element and a target analyte (e.g. activatable element) under conditions that allow specific binding to occur.

In some embodiments, the target binding operation is performed in a buffer containing a "blocking reagent" that reduces non-specific binding. In some embodiments, the blocking reagent is milk. In some embodiments, the blocking reagent is fetal bovine serum. In some embodiments, the blocking reagent is bovine serum albumin. In some embodiments, the blocking reagent is goat serum.

In some embodiments, the target binding operation is performed with the detection complex in molar excess of the target analyte.

In some embodiments, the target binding operation is performed using a sample of suspended cells. In some embodiments, the target binding operation is performed using a sample of adherent cells. In some embodiments, the target binding operation is performed using a sample fixed to a solid support. Exemplary solid supports include polystyrene, dextran, acrylamide, ELISA plates, polystyrene beads, and glass, etc. microscope slides. In some embodiments, the target binding operation is performed using a sample of tissue, such as a section of formalin-fixed tissue. In some embodiments, the target binding operation is performed using a sample of live cells. In some embodiments, the target binding operation is performed using a sample of fixed cells. In some embodiments, the target binding operation is performed using a sample of permeabilized cells. In some embodiments, the target binding operation is performed using the lysate of a sample of cells. In some embodiments, the target binding operation is performed with an extracellular protein as the target analyte. In some embodiments, the target binding operation is performed with an intracellular protein as the target analyte. In some embodiments, the target binding operation is performed with an activatable element as the target analyte, as disclosed in U.S. Pat. Nos. 7,381,535 and 7,393,656 and U.S. Ser. Nos. 10/193,462; 11/655,785; 11/655,789; 11/655,821; 11/338,957, 61/048,886; 61/048,920; 61/048,657; 61/079,766, and 61/085,789. All of these references are incorporated into the present disclosure as well as those cited below.

In some embodiments the sample preparation steps are carried out under different temperatures whereas the fixation, permeabilization, binding and staining reactions are carried out under a different set of temperatures (each of which might be different than the others).

(iv) Unbound Detection Complex Removal Operation

It is desirable to remove unbound detection complexes from a sample prior to measurement. An objective of this operation is to ensure that only detection complexes bound to a target analyte are measured, and thereby ensure that the intensity of the signal will be correlated to the abundance of said target analyte. As used herein, the term "wash" and grammatical equivalents thereof refer to the process of removing unbound detection complexes from a sample prior to measurement. Methods of washing samples are well known to those skilled in the art, and generally involve diluting the labeling reaction with an excess of buffer solution, and selectively purifying the sample away from any unbound labeling elements. In some embodiments of the invention, washing a particulate sample, such as live cells, is performed by resuspension in aqueous buffer followed by centrifugation and disposal of the supernatant. In some embodiments of the invention, washing an immobilized sample, such as adherent cells, is performed by overlaying the sample with an aqueous buffer then discarding said buffer.

5. Measurement of Detection Complexes

In practicing the methods of this invention, the measurement of the abundance of one or more assembled detection complexes can be carried out by a person, such as a technician in the laboratory. Alternatively, the measurement of the abundance of one or more assembled detection complexes can be carried out using automated systems. In either case, the measurement of the abundance of one or more assembled detection complexes for use according to the methods of this invention is performed according to standard techniques and protocols well-established in the art.

One or more assembled detection complexes can be detected and/or quantified by any method that detects and/or quantifies the presence of the assembled detection complex of interest. Such methods may include radioimmunoassay (RIA) or enzyme linked immunoabsorbance assay (ELISA), immunohistochemistry, immunofluorescent histochemistry with or without confocal microscopy, Raman spectroscopy, X-ray autoradiography, X-ray radiography, luminescence spectrometry, reversed phase assays, homogeneous enzyme immunoassays, and related non-enzymatic techniques, Western blots, whole cell staining, immunoelectron microscopy, nucleic acid amplification, gene array, protein array, mass spectrometry, patch clamp, 2-dimensional gel electrophoresis, differential display gel electrophoresis, microsphere-based multiplex protein assays, label-free cellular assays and flow cytometry, etc. U.S. Pat. No. 4,568,649 describes ligand detection systems, which employ scintillation counting. These techniques are particularly useful for modified protein parameters. Cell readouts for proteins and other cell determinants can be obtained using fluorescent or otherwise tagged reporter molecules. Microscopy methods are useful for measuring parameters in a morphological context. Flow cytometry methods are useful for measuring intracellular parameters.

When using fluorescent labeled components in the methods and compositions of the present invention, it will recognized that different types of fluorescent monitoring systems, e.g., Cytometric measurement device systems, can be used to practice the invention. In some embodiments, flow cytometric systems are used or systems dedicated to high throughput screening, e.g. 96 well or greater microtiter plates. See U.S. Ser. No. 61/108,803. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation that has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. In general, known robotic systems and components can be used.

Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remade et al., Proc. Natl. Sci. USA (2000) 18:553-8, each expressly incorporated herein by reference) as well as confocal microscopy.

In general, flow cytometry involves the passage of individual cells through the path of a laser beam. The scattering the beam and excitation of any fluorescent molecules attached to, or found within, the cell is detected by photomultiplier tubes to create a readable output, e.g. size, granularity, or fluorescent intensity.

The detecting, sorting, or isolating step of the methods of the present invention can entail fluorescence-activated cell sorting (FACS) techniques, where FACS is used to select cells from the population containing a particular surface marker, or the selection step can entail the use of magnetically responsive particles as retrievable supports for target cell capture and/or background removal. A variety of FACS systems are known in the art and can be used in the methods of the invention (see e.g., WO99/54494, filed Apr. 16, 1999; U.S. Ser. No. 20010006787, filed Jul. 5, 2001, each expressly incorporated herein by reference).

In some embodiments, a FACS cell sorter (e.g. a FACSVantage™, LSRII, or Canto Cell Sorter, Becton Dickinson Immunocytometry Systems, San Jose, Calif.) is used to sort and collect cells based on the presence or absence of an assembled detection complex. By imparting an electromagnetic charge to droplets containing the positive cells, the cells can be separated from other cells. The positively selected cells can then be harvested in sterile collection vessels. These cell-sorting procedures are described in detail, for example, in the FACSVantage™. Training Manual, with particular reference to sections 3-11 to 3-28 and 10-1 to 10-17, which is hereby incorporated by reference in its entirety for the above instruments.

In another embodiment, positive cells can be sorted using magnetic separation of cells based on the presence of an assembled detection complex. In such separation techniques, cells to be positively selected are first contacted with an assembled detection complex comprising retrievable particles (e.g., magnetically responsive particles). The cell can then be physically separated from non-positive or non-labeled cells, for example, using a magnetic field. When using magnetically responsive particles, the positive or labeled cells can be retained in a container using a magnetic filed while the negative cells are removed. These and similar separation procedures are described, for example, in the Baxter Immunotherapy Isolex training manual which is hereby incorporated in its entirety.

In some embodiments, one or more cells are contained in a well of a 96 well plate or other commercially available multi-well plate. In an alternate embodiment, the reaction mixture or cells are in a cytometric measurement device. Other multi-well plates useful in the present invention include, but are not limited to 384 well plates and 1536 well plates. Still other vessels for containing the reaction mixture or cells and useful in the present invention will be apparent to the skilled artisan.

In some embodiments, the abundance of an assembled detection complex is measured using Inductively Coupled Plasma Mass Spectrometer (ICP-MS). A binding element that has been labeled with a specific element binds to the assembled detection complex. When the cell is introduced into the ICP, it is atomized and ionized. The elemental composition of the cell, including the labeled binding element that is bound to the assembled detection complex, is measured. The presence and intensity of the signals corresponding to the labels on the binding element indicates the abundance of the assembled detection complex on that cell (Tanner et al. Spectrochimica Acta Part B: Atomic Spectroscopy, (2007), 62(3): 188-195.).

In some embodiments the 'flow cytometer' is a microfluidic device where the cell measurements, or some of the measurements of the cell's contents, are carried out in channels devised to direct cells past detection devices in parallel sets of multiple channels. See U.S. Pat. Nos. 7,378,280; 7,294,503; 7,294,298; and 6,830,936.

In some embodiments the cells, or some portion of their contents, are sonically encapsulated within individual droplets of liquid and interrogated with detection devices designed to measure each individual droplet's characteristics and the materials within such droplets.

In some embodiments, confocal microscopy can be used to detect assembled probe complexes on individual cells. Confocal microscopy relies on the serial collection of light from spatially filtered individual specimen points, which is then electronically processed to render a magnified image of the specimen. The signal processing involved confocal microscopy has the additional capability of detecting labeled binding elements within single cells, accordingly in this embodiment the cells can be labeled with one or more binding elements. In some embodiments the binding elements used in connection with confocal microscopy are antibodies conjugated to fluorescent labels, however other binding elements, such as other proteins or nucleic acids are also possible.

Flow cytometry or capillary electrophoresis formats can be used for individual capture of magnetic and other beads, particles, cells, and organisms.

Flexible hardware and software allows instrument adaptability for multiple applications. The software program modules allow creation, modification, and running of methods. The system diagnostic modules allow instrument alignment, correct connections, and motor operations. Customized tools, labware, and liquid, particle, cell and organism transfer patterns allow different applications to be performed. Databases allow method and parameter storage. Robotic and computer interfaces allow communication between instruments.

In some embodiments, the methods of the invention include the use of liquid handling components. The liquid handling systems can include robotic systems comprising any number of components. In addition, any or all of the steps outlined herein may be automated; thus, for example, the systems may be completely or partially automated. See U.S. Ser. No. 61/108,803.

As will be appreciated by those in the art, there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation. Additional examples of automation, automated sample collection and analysis are disclosed in U.S. Ser. Nos. 61/048,657 which is hereby incorporated by reference in its entirety and 61/108,803.

In some embodiments, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In some embodiments, platforms for multi-well plates, multi-tubes, holders, cartridges, minitubes, sonic levitation and encapsulation, deep-well plates, microfuge tubes, cryovials, square well plates, filters, chips, microchannel chips, microfluidics chips, optic fibers, beads, and other solid-phase matrices or platform with various volumes are accommodated on an upgradeable modular platform for additional capacity. This modular platform includes a variable speed orbital shaker, and multi-position work decks for source samples, sample and reagent dilution, assay plates, sample and reagent reservoirs, pipette tips, and an active wash station. In some embodiments, the methods of the invention include the use of a plate reader.

In some embodiments, thermocycler and thermoregulating systems are used for stabilizing the temperature of heat exchangers such as controlled blocks or platforms to provide accurate temperature control of incubating samples from 0° C. to 100° C.

In some embodiments, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In some embodiments, useful detectors include a microscope(s) with multiple channels of fluorescence; plate readers to provide fluorescent, ultraviolet and visible spectrophotometric detection with single and dual wavelength endpoint and kinetics capability, fluorescence resonance energy transfer (FRET), luminescence, quenching, two-photon excitation, and intensity redistribution; CCD cameras to capture and transform data and images into quantifiable formats; and a computer workstation.

In some embodiments, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

6. Removing Labels from Bound Detection Complexes

In some embodiments, assembled detection complexes may be disassembled following detection without destroying the sample. An objective of this strategy is to enable the reuse of a sample and when it is desirable to measure more analytes on a single sample than can be detected simultaneously by the instrument. In some embodiments, enzymatic or catalytic digestion of oligonucleotide joining elements may be performed after a first detection operation. In some embodiments, the enzyme is a non-specific endonuclease. In some embodiments, the enzyme is a sequence-specific endonuclease. Exemplary enzymes suitable for this purpose include: Deoxyribonuclease I, which cleaves all double-stranded oligonucleotides; Restriction endonuclease BamHI, would cleave only bound, double-stranded joining elements with a specific sequence. In some embodiments, oligonucleotide joining element sequences are selected to allow digestion of a set of assembled detection complexes by a specific class of restriction endonucleases.

EXAMPLES

Example 1

Phospho-Specific Flow Cytometry Using Oligo-Conjugated Dyes and Antibodies

Selection of proximal joining elements: Three species of 100 bp ssDNA oligonucleotides are selected having less than 25% sequence identity, and synthesized with a 5' terminal amino group. These oligonucleotides shall be referred to herein as oligos A, B, and C.

Selection of distal joining elements: Three species of 100 bp ssDNA oligonucleotides are selected with 100% sequence complementary to oligos A, B, and C described above, and synthesized with a 3' terminal amino group. These shall be referred to herein as oligos A', B' and C'.

Selection of binding elements: Three species of unlabeled, purified, phospho-specific, monoclonal antibodies are chosen with affinity for pStat1, pStat3, and pStat5.

Selection of labeling elements: Three species of fluorescent dyes are selected having minimally overlapping emission spectra, such that all three dyes can be measured simultaneously on a flow cytometer, referred to herein as dyes X, Y and Z. Three exemplary dyes are AlexaFluor488, AlexaFluor647, and Pacific Blue dyes from Invitrogen. The dyes are purchased covalently bound to amine-reactive succinimidyl esters.

Synthesis of detection complexes: Each class of proximal oligonucleotide is conjugated to a different class of antibody, linking the 5' end of the oligonucleotide to the antibody by means of SATA chemistry, described by Hendrickson et al. (1995). Three separate reactions yield three classes of DNA-conjugated antibodies, as shown below:
 pStat1 antibody: Oligo A
 pStat3 antibody: Oligo B
 pStat5 antibody: Oligo C Each oligonucleotide is conjugated to a different dye in the following reaction:
 1 μg/uL amino-modified oligonucleotide
 1 μg/μL amine-reactive dye
 in 0.1 M sodium borate buffer, pH 8.5
 . . . Incubating 6 hours while rotating at 200 RPM at room temperature The oligonucleotides and dyes are paired as follows:
 Dye X: Oligo A'
 Dye Y: Oligo B'
 Dye Z: Oligo C'

The dye-conjugated oligonucleotides are purified to remove unbound dye by means of reverse-phase HPLC following protocols described in *HPLC of Macromolecules: A Practical Approach*, $2^{nd}$ edition, Oxford University Press (1998). The result is three classes of DNA-conjugated dyes.

Timing: For this example, elements will be conjugated (thus creating assembled detection complexes) on the day of the assay, but before of binding to the target analyte. This decision must be made depending on the demands and circumstances of each assay, and is influenced by factors such as the binding affinity of the joining elements, the stability of the target analyte, the time required to conjugate the joining elements, and the buffer conditions suitable for the joining element self-assembly operation versus the target binding operation.

Joining element self-assembly: A cocktail of three DNA-conjugated antibodies is conjugated to three DNA-conjugated dyes in the multiplex reaction below, referred to herein as the labeling cocktail:
 5 μg DNA-conjugated p-Stat1 antibody/A
 5 μg DNA-conjugated p-Stat3 antibody/B
 5 μg DNA-conjugated p-Stat5 antibody/C
 1 μg DNA-conjugated Dye X/A'
 1 μg DNA-conjugated Dye Y/B'
 1 μg DNA-conjugated Dye Z/C'
 in 1 mL of hybridization buffer (1 M NaCl, 10 mM Tris-HCl, 1 mM EDTA, 0.01% SDS)
 . . . Incubating 2 hours at room temperature.

Sample preparation: One million U937 cells are stimulated 15 minutes with a cocktail of IFN-γ, G-CSF and GM-CSF (20 ng/mL each), as described in Krutzik et al. Intracellular phospho-protein staining technique for flow cytometry: Monitoring single cell signaling events. Cytometry (2003) vol. 55A (2) pp. 61-70. One million U937 cells mock stimulated with PBS for 15 minutes are used as a control. Both samples are fixed in 1.6% paraformaldehyde for 10 minutes at room temperature then washed and resuspended in 2 mL ice-cold methanol for 20 minutes. Each sample is washed and resuspended in 90 μL cell staining media (PBS, 0.5% bovine serum albumin, 0.02% sodium azide).

Target binding: For each sample, 10 μL of the labeling cocktail is added to the existing 90 μL volume and mixed thoroughly. Samples are incubated 30 minutes at room temperature in the dark.

Unbound antibody is removed by washing the cells twice with 1 mL cell staining media.

Measurement of detection complexes: The amount of fluorescent dye bound to each cell is measured using a flow cytometer (i.e. Becton-Dickinson LSR-II). The amount of fluorescent Dye X correlates to the amount of pStat1 antibody bound to the cell, thereby reflecting the amount of the phosphorylated Stat1 present in the cell. The same interpretation applies for the other pairs of dyes and antibodies (i.e. p-Stat3/Dye Y and p-Stat5/Dye Z).

Example 2

Immunofluorescence Microscopy Using Oligo-Conjugated Dyes and Antibodies

Detection complex design: In this example, four target analytes are to be measured on a single section of human breast tissue mounted on a glass microscope slide. To illustrate the flexibility of assay design afforded by the invention, the microscope used in the example is only capable of measuring two parameters simultaneously. Two staining procedures will be performed, each using the same two classes of labeling elements. The first set of labeling elements will be removed by a stripping operation prior to staining with the second set of detection complexes.

Selection of proximal joining elements: Four species of 100 bp ssDNA oligonucleotides are selected having less than 25% sequence identity, and synthesized with a 5' terminal amino group. These oligonucleotides shall be referred to herein as oligos A, B, C and D.

Selection of distal joining elements: Four species of 100 bp ssDNA oligonucleotides are selected with 100% sequence complementary to oligos A, B, and C described above, and synthesized with a 3' terminal amino group. These shall be referred to herein as oligos A', B', C' and D'.

Selection of binding elements: Four species of unlabeled, purified, monoclonal antibodies are chosen with affinity for human HLA-DR, CD24, CD44 and CD66.

Selection of labeling elements: Two species of fluorescent dyes are selected having minimally overlapping emission spectra, such that both dyes can be measured simultaneously on an epifluorescence microscope. These dyes are referred to herein as dyes X and Y. Two exemplary dyes are AlexaFluor488 and AlexaFluor647 dyes from Invitrogen. The dyes are purchased covalently bound to amine-reactive succinimidyl esters. In this example, an epifluorescence microscope equipped with a mercury arc lamp as the source of illumination, appropriate filters for exciting the two dyes and capturing the emission spectra, and a cooled CCD camera for measuring the photons shall be used.

Synthesis of detection complexes: Each class of proximal oligonucleotide is conjugated to a different class of antibody, linking the 5' end of the oligonucleotide to the antibody by means of SATA chemistry, described by Hendrickson et al. (1995). Four separate reactions yield four classes of DNA-conjugated antibodies, as shown below:

HLA-DR antibody: Oligo A
CD24 antibody: Oligo B
CD44 antibody: Oligo C
CD66 antibody: Oligo D Each oligonucleotide is conjugated to a different dye in the following reaction:

1 µg/uL amino-modified oligonucleotide
1 µg/µL amine-reactive dye
in 0.1 M sodium borate buffer, pH 8.5
... Incubating 6 hours while rotating at 200 RPM at room temperature The oligonucleotides and dyes are paired as follows. Note that the dyes are each used twice, but every dye is conjugated to a different oligonucleotide:

Dye X: Oligo A'
Dye Y: Oligo B'
Dye X: Oligo C'
Dye Y: Oligo D'

The dye-conjugated oligonucleotides are purified to remove unbound dye by means of reverse-phase HPLC following protocols described in *HPLC of Macromolecules: A Practical Approach,* 2nd edition, Oxford University Press (1998). The result is four classes of DNA-conjugated dyes.

Timing: For this example, elements will be allowed to self-assemble (thus creating assembled detection complexes) after the binding elements have bound their target analytes. Two distinct staining and detection operations will be performed, separated by a stripping operation to remove labels from the first staining operation.

Sample preparation: A biopsy of human breast epithelial carcinoma is fixed in formalin and embedded in paraffin following standard clinical histology protocols. A 50 micron section is mounted on a glass microscope slide and prepared for staining by the following steps:

1. Incubate sections are washed three times in xylene for 5 minutes each.
2. Incubate sections are washed twice in 100% ethanol for 10 minutes each.
3. Incubate sections are washed twice in 95% ethanol for 10 minutes each.
4. Sections are rinsed twice in distilled water for 5 minutes each.
5. Slides are placed in room temperature 10 mM sodium citrate buffer pH 6.0.
6. Slides are brought to 95-99° C. in sodium citrate buffer using a microwave and maintained at that temperature for 10 minutes.
7. Slides are cooled for 30 minutes on bench top.
8. Sections are rinsed in distilled water three times for 5 minutes each.
9. Sections are rinsed in phosphate buffered saline (PBS) for 5 minutes.
10. Sections are blocked in PBS supplemented with 5% fetal calf serum for 60 minutes at 22° C. in a humid chamber.

Target binding (first round): The following cocktail of two prepared detection complex components (antibody/oligo conjugates) is prepared:

50 ng DNA-conjugated HLA-DR antibody/A
50 ng DNA-conjugated CD24 antibody/B
in 100 µL of staining media (PBS, 0.3% Triton X-100).

The cocktail is applied to the section and incubated 30 minutes at room temperature in a humidified chamber. Unbound detection complexes are removed by rinsing with PBS three times, 5 minutes each.

Joining element self-assembly (first round): The following cocktail of two prepared detection complex components (dye/oligo conjugates) is prepared:

100 ng DNA-conjugated Dye X/A'
100 ng DNA-conjugated Dye Y/B'
in 100 µL of hybridization buffer (1 M NaCl, 10 mM Tris-HCl, 1 mM EDTA).

The cocktail is applied to the section and incubated 15 minutes at room temperature in a humidified chamber. Unbound detection complexes are removed by rinsing once with hybridization buffer, then twice with PBS, 5 minutes each.

Measurement of detection complexes (first round): The amount of fluorescent dye bound to the section is measured using an epifluorescence microscope and captured with a digital camera. The amount of fluorescent Dye X correlates to the amount of HLA-DR antibody bound to the section, thereby reflecting the amount of the target analyte at that location. The same interpretation applies for presence of CD24 antibody reflected by the abundance of Dye Y. Images are captured covering the entire slide or the areas of interest, preferably using an automatic motorized stage. For each image, the Cartesian coordinates are recorded with the optical data so the same location can be compared between two image acquisition sessions.

Bound probe removal: Bound, assembled detection complexes are removed from the section by means of enzymatic digestion of the hybridized cognate joining elements. A solution of deoxyribonuclease I (DNAse) is prepared in 100 µL DNAse digestion buffer (10 mM Tris-HCl, 2.5 mM $MgCl_2$, 0.5 mM $CaCl_2$, pH 7.6) at a final concentration of 20 U/mL. The section is washed once in DNAse digestion buffer. The DNAse solution is applied to the section and incubated 20 minutes at room temperature in a humidified chamber at 37° C. The slide is incubated in DNAse stop buffer (10 mM Tris-HCl, 5 mM EDTA), 10 minutes at 75° C., then washed again in DNAse stop buffer. The slide is then washed in staining media. It may be useful to briefly examine the slide on the epifluorescence microscope to confirm that all labels have been removed. If not all labels are removed, the DNAse digestion and washing steps are repeated.

Target binding (second round): The following cocktail of two prepared detection complex components (antibody/oligo conjugates) is prepared:

50 ng DNA-conjugated CD44 antibody/C
50 ng DNA-conjugated CD66 antibody/D
in 100 µL of staining media (PBS, 0.3% Triton X-100).

The cocktail is applied to the section and incubated 30 minutes at room temperature in a humidified chamber. Unbound detection complexes are removed by rinsing with PBS three times, 5 minutes each.

Joining element self-assembly (second round): The following cocktail of two prepared detection complex components (dye/oligo conjugates) is prepared:

100 ng DNA-conjugated Dye X/C'
100 ng DNA-conjugated Dye Y/D'
in 100 µL of hybridization buffer (1 M NaCl, 10 mM Tris-HCl, 1 mM EDTA).

The cocktail is applied to the section and incubated 15 minutes at room temperature in a humidified chamber. Unbound detection complexes are removed by rinsing once with hybridization buffer, then twice with PBS, 5 minutes each.

Measurement of detection complexes (second round): The amount of fluorescent dye bound to the section is measured using an epifluorescence microscope and captured with a digital camera. The amount of fluorescent Dye X correlates to the amount of CD44 antibody bound to the section, thereby reflecting the amount of the target analyte at that location. The same interpretation applies for presence of CD66 antibody reflected by the abundance of Dye Y. New images are captured at each location as the used in the first image acquisition session.

Data analysis: Images from a single session may be stitched together using appropriate image-analysis software, such as MetaMorph software by Molecular Devices. Stitched images from both sessions may be overlaid using different colors to represent each fluorescent analysis channel. Alternatively, many smaller overlays may be constructed using each image from the two sessions, matching each pair of images using the Cartesian coordinates, and overlaying the colors as before. In this fashion, the co-localization of four target analytes may be assessed on the same physical sample, using a microscope that can only capture two fluorescent channels simultaneously.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition of distinguishable assembled detection complexes, wherein an assembled detection complex comprises:
   a binding element for an activatable element;
   a plurality of joining elements;
   a distinguishable labeling element;
   wherein the binding elements are non-covalently attached to specific distinguishable labeling elements in the assembled detection complexes through the joining elements, the distinguishable labeling elements have minimal overlapping emission spectra when combined with other different assembled detection complexes in the composition.

2. A composition having a plurality of distinguishable assembled detection complexes, comprising:
   (i) a plurality of different antibodies which bind a plurality of different activatable elements,
   (ii) a plurality of distinguishable labeling elements matched to the plurality of different antibodies to form a distinguishable assembled detection complexes;
   (iii) a plurality of joining elements, comprising nucleic acids, selected to join specific binding elements to specific distinguishable labeling elements;
   wherein the assembled detection complexes have the formula antibody joining elements-labeling element and wherein the antibodies are non-covalently joined to the distinguishable labeling elements in the assembled detection complexes and the plurality of distinguishable labeling elements have minimal overlapping emission spectra.

3. The composition of claim 1 wherein said binding element is a peptide, a polypeptide, an oligopeptide, or an antibody.

4. The composition of claim 1 wherein said joining elements are independently selected from the group consisting of leucine zippers, polymers, peptide loops, nucleic acids, DNA, RNA and peptide nucleic acids.

5. The composition of claim 1 or 2 wherein more than one the distinguishable labeling element is attached to said joining elements.

6. The composition of claim 1 or 2 wherein said labeling element is an element selected from the group consisting of small molecule fluorophores, proteinaceous fluorophores, chromogenic dyes, luminescent dyes, chelated or caged lanthanides, isotope tags, mass tags, and nanoparticles.

7. The composition of claim 1 or 2 wherein the labeling element comprises a small molecule fluorophore or a proteinaceous fluorophore.

8. The composition of claim 1 or 2 wherein one of the joining elements is an oligonucleotide or a nucleic acid having about 10 to about 100 bases in length.

9. The composition of claim 1 or 2 wherein one of said joining elements is covalently attached to said binding element.

10. The composition of claim 1 or 2 wherein said activatable element is a phosphoprotein.

11. A composition in accordance with claim 1 wherein the joining element is a nucleic acid.

12. The composition of claim 1 or 2 wherein the joining elements are designed to attach one specific binding element to one specific labeling element to the exclusion of other binding elements or labeling elements through the use of a first joining element, wherein said first joining element comprises a first oligonucleotide attached to said binding element, and wherein said first oligonucleotide comprises a first complementary oligonucleotide region;

a second joining element comprising a second oligonucleotide, wherein said second oligonucleotide comprises a labeling element, and wherein said second oligonucleotide comprises a second complementary oligonucleotide region; and a third joining element comprising a third oligonucleotide, wherein said third oligonucleotide comprises a third complementary oligonucleotide region and a fourth complementary oligonucleotide region, wherein said third complementary oligonucleotide region is complementary to said first complementary oligonucleotide region in said first joining element and wherein said fourth complementary oligonucleotide region is complementary to said second complementary oligonucleotide region in said second joining element.

13. The composition of claim 1 or 2 further comprising a first joining element which comprises a first oligonucleotide attached to said binding element, and wherein said first oligonucleotide comprises a first complementary oligonucleotide region;

a second joining element comprising a second oligonucleotide, wherein said second oligonucleotide comprises a labeling element, and wherein said second oligonucleotide comprises a second complementary oligonucleotide region, wherein said second complementary oligonucleotide region is complementary to said first complementary oligonucleotide region in said first joining element.

14. The composition of claim 1 or 2 wherein the joining elements hold the binding elements and labeling elements together with a dissociation constant of less than about $10^{-4}$ to $10^{-9} M^{-1}$.

15. The composition of claim 1 or 2 wherein the joining elements hold the binding elements and labeling elements together with a dissociation constant of less than about $10^{-5}$ to $10^{-9} M^{-1}$.

16. The composition of claim 1 or 2 wherein there are three different assembled detection complexes present in the composition.

17. A method for preparing a plurality of different assembled detection complexes comprising:
providing a plurality of different binding elements, wherein said binding elements are directed against different activatable elements;
providing a plurality of distinguishable labeling elements with minimal overlapping emission spectra to be specifically attached to the plurality of binding elements to form an assembled detection complex;
providing a plurality joining elements to join the binding elements to the labeling elements;
matching a binding element with a distinguishable labeling element to form a specific assembled detection complex which has minimal overlapping emission spectra when combined with other assembled detection complexes; and
selectively joining the assembled detection complexes.

18. A method for preparing a plurality of different assembled detection complexes comprising:
providing a plurality of different antibodies which bind specific activatable elements;
providing a plurality of distinguishable labeling elements with minimal overlapping emission spectra, to be attached to the plurality of antibodies to form assembled detection complexes;
providing a plurality of joining elements, which comprise nucleic acids, to join the binding elements to the labeling elements wherein the process for attachment for each assembled detection complex is as follows:
matching a specific antibody with a specific labeling element which has minimal overlapping emission spectra when combined with other labeling elements in other assembled detection complexes; and
selectively assembling the plurality of assembled detection complexes.

19. The method in accordance of claim 17 or 18 wherein said joining elements comprises a first joining element, wherein said first joining element comprises a first oligonucleotide attached to said binding element, and wherein said first oligonucleotide comprises a first complementary oligonucleotide region;

a second joining element comprising a second oligonucleotide, wherein said second oligonucleotide comprises a labeling element, and wherein said second oligonucleotide comprises a second complementary oligonucleotide region; and a third joining element comprising a third oligonucleotide, wherein said third oligonucleotide comprises a third complementary oligonucleotide region and a fourth complementary oligonucleotide region, wherein said third complementary oligonucleotide region is complementary to said first complementary oligonucleotide region in said first joining element and wherein said fourth complementary oligonucleotide region is complementary to said second complementary oligonucleotide region in said second joining element.

20. The method in accordance of claim 17 or 18 wherein said joining elements comprise a first joining element, wherein said joining element comprises a first oligonucleotide attached to said binding element, and wherein said first oligonucleotide comprises a first complementary oligonucleotide region;

a second joining element comprising a second oligonucleotide, wherein said second oligonucleotide comprises a labeling element, and wherein said second oligonucleotide comprises a second complementary oligonucleotide region, wherein said second complementary oligonucleotide region is complementary to said first complementary oligonucleotide region in said first joining element.

21. A method of detecting the presence or absence of a plurality of different activatable elements in a sample comprising:
providing a plurality of assembled detection complexes, comprising:
a plurality of binding elements directed against different activatable elements;
a plurality of distinguishable labeling elements with minimal overlapping emission spectra to be specifically joined to the plurality of binding elements to form assembled detection complexes; and
a plurality of nucleic acid joining elements to specifically join the binding elements and labeling elements;
selecting a binding element to be joined to a distinguishable labeling element to form a specific assembled detection complex; and
mixing a plurality of assembled detection complexes with the different activatable elements; and measuring binding.

22. The method of claim 21 wherein the joining elements are oligonucleotides and joining the binding element and the labeling element may occur before or after mixing with the activatable element.

23. The method of claim 21 wherein each of the binding elements of the assembled detection complexes comprises an antibody and a plurality of joining elements which comprise:
a first joining element, wherein said first joining element comprises a first oligonucleotide attached to said binding element, and wherein said first oligonucleotide comprises a first complementary oligonucleotide region;
a second joining element comprising a second oligonucleotide, wherein said second oligonucleotide comprises a second complementary oligonucleotide region; and
a third joining element comprising a third oligonucleotide, wherein said third oligonucleotide comprises a third complementary oligonucleotide region and a fourth complementary oligonucleotide region, wherein said third complementary oligonucleotide region is complementary to said first complementary oligonucleotide region in said first joining element and wherein said fourth complementary oligonucleotide region is complementary to said second complementary oligonucleotide region in said second joining element;
a labeling element; and
wherein the measuring step uses a flow cytometer or mass spectrometer.

24. A method in accordance with claim 2 wherein the joining element is a nucleic acid.

25. A kit for the preparation of a plurality of distinguishable assembled detection complexes, comprising:
(i) a plurality of different binding elements which bind a plurality of different activatable elements,
(ii) a plurality of distinguishable labeling elements for attachment to the plurality of binding elements; and
(iii) a plurality of joining elements to selectively join the binding elements to the labeling elements to form distinguishable assembled detection complexes, wherein the labeling elements have minimal overlapping emission spectra when combined in a mixture of a plurality of distinguishable assembled detection complexes.

26. A kit in accordance with claim 25 wherein the joining element is a nucleic acid.

27. A kit in accordance with claim 26 wherein the binding element is an antibody.

* * * * *